United States Patent
Stasi et al.

(10) Patent No.: US 9,174,977 B2
(45) Date of Patent: Nov. 3, 2015

(54) 2-AZABICYCLO[4.1.0]HEPTANE DERIVATIVES AS OREXIN RECEPTOR ANTAGONISTS FOR THE TREATMENT OF CERTAIN DISORDERS

(71) Applicant: Rottapharm Biotech S.r.l., Monza (IT)

(72) Inventors: Luigi Piero Stasi, Monza (IT); Lucio Claudio Rovati, Monza (IT)

(73) Assignee: Rottapharm Biotech S.R.L., Monza (IT)

( * ) Notice: Subject to any disclaimer, the term of this patent is extended or adjusted under 35 U.S.C. 154(b) by 0 days.

(21) Appl. No.: 14/386,109

(22) PCT Filed: Mar. 18, 2013

(86) PCT No.: PCT/EP2013/055548
§ 371 (c)(1),
(2) Date: Sep. 18, 2014

(87) PCT Pub. No.: WO2013/139730
PCT Pub. Date: Sep. 26, 2013

(65) Prior Publication Data
US 2015/0065523 A1   Mar. 5, 2015

(30) Foreign Application Priority Data
Mar. 19, 2012 (IT) .............................. MI2012A0424

(51) Int. Cl.
   *C07D 401/04*   (2006.01)
   *C07D 405/00*   (2006.01)
   *C07D 417/14*   (2006.01)
   *C07D 401/14*   (2006.01)
   *C07D 401/10*   (2006.01)

(52) U.S. Cl.
   CPC ............ *C07D 417/14* (2013.01); *C07D 401/10* (2013.01); *C07D 401/14* (2013.01)

(58) Field of Classification Search
   None
   See application file for complete search history.

(56) References Cited

U.S. PATENT DOCUMENTS

| | | | |
|---|---|---|---|
| 3,282,927 A | 11/1966 | Montzka | |
| 8,133,908 B2 * | 3/2012 | Alvaro et al. | ................. 514/354 |
| 8,859,608 B2 | 10/2014 | Stasi et al. | |
| 2012/0040991 A1 * | 2/2012 | Amantini et al. | ........ 514/252.02 |
| 2014/0357653 A1 | 12/2014 | Stasi et al. | |

FOREIGN PATENT DOCUMENTS

| | | |
|---|---|---|
| EP | 2275421 A1 | 1/2011 |
| WO | WO 03/051368 A1 | 6/2003 |
| WO | WO 2006/127550 A1 | 11/2006 |
| WO | WO 2008/038251 A2 | 4/2008 |
| WO | WO 2008/081399 A2 | 7/2008 |
| WO | WO 2008/101665 A1 | 8/2008 |
| WO | WO 2008/139416 A1 | 11/2008 |
| WO | WO 2008/147518 A1 | 12/2008 |
| WO | WO 2009/016564 A3 | 2/2009 |
| WO | WO 2010/048016 A1 | 4/2010 |
| WO | WO 2010/051238 A1 | 5/2010 |
| WO | WO 2010/060470 A1 | 6/2010 |
| WO | WO 2010/060471 A1 | 6/2010 |
| WO | WO 2010/063662 A1 | 6/2010 |
| WO | WO 2010/063663 A1 | 6/2010 |
| WO | WO 2010/122151 A1 | 10/2010 |
| WO | WO2010/132601 A1 | 11/2010 |
| WO | WO 2011/006960 A1 | 1/2011 |
| WO | WO 2011/076747 A1 | 6/2011 |
| WO | WO 2012/104338 A1 | 8/2012 |
| WO | WO 2013/092893 A1 | 6/2013 |

OTHER PUBLICATIONS

Aston-Jones et al., 2009, "Role of lateral hypothalamic orexin neurons in reward processing and addiction," Neuropharmacology, 56:112-121.
Brisbare-Roch et al., 2009, "Promotion of sleep by targeting the orexin system in rats, dogs and humans," Nature Medicine (Advance Online Publication), 1-6.
Chemelli et al., 1999, "Narcolepsy in orexin Knockout Mice: Molecular Genetics of Sleep Regulation," Cell, 98:437-451.
Chen et al., 2000, "Pressor effects of orexins injected intracisternally and to rostral ventrolateral medulla of anesthetized rats," Am. J. Physiol. Reg. Integrative Comp. Physiol., 278:R692-R697.
Dayas et al., 2008, "Stimuli Linked to Ethanol Availability Activate Hypothalamic CART and Orexin Neurons in a Reinstatement Model of Relapse," Biol. Psychiatry, 63:152-157.

(Continued)

*Primary Examiner* — Heidi Reese
(74) *Attorney, Agent, or Firm* — Jones Day

(57) ABSTRACT

The present invention provides compounds of formula (I) including stereoisomers or a racemate or a mixture or a pharmaceutically acceptable salt thereof: wherein X is NH, or O; Q is 5-6 membered heteroaryl group, which may be substituted by one or more substituents independently selected from a group consisting of: C1-C4 alkyl, halogen, halo C1-C4 alkyl, C1-C4 alkoxy, CN; A is phenyl or a 5-6 heteroaryl group, which may be substituted by one or more substituents independently selected from a group consisting of: C1-C4 alkyl, halogen, halo C1-C4 alkyl, C1-C4 alkoxy, CN; B may assume different meanings from A and is phenyl or a 5-6 membered heteroaryl group, which may be substituted by one or more substituents independently selected from a group consisting of: C1-C4 alkyl, halogen, halo C1-C4 alkyl, C1-C4 alkoxy, CN; and processes for their preparation, pharmaceutical compositions containing them and their use as dual antagonists of the Orexin 1 and Orexin 2 receptors.

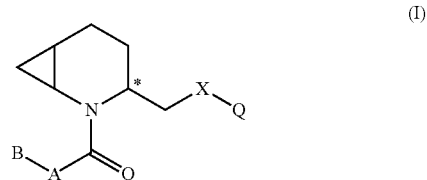

(I)

7 Claims, No Drawings

(56) References Cited

OTHER PUBLICATIONS

Dugovic et al., 2009, "Blockade of Orexin-1 Receptors Attenuates Orexin-2 Receptor Antagonism-Induced Sleep Promotion in the Rat," The Journal of Pharmacology and Experimental Therapeutics, 330:142-151.
Fargeas et al., 2003, "Nitration of Heteroaryltrimethyltins by Tetranitromethane and Dinitrogen Tetroxide: Mechanistic Aspects, Scope and Limitations," Eur. J. Org. Chem., 1711-1721.
Fleisher et al., 1996, "Improved oral drug delivery: solubility limitations overcome by the use of prodrugs," Advanced Drug Delivery Reviews, 19:115-130.
Georgescu et al., 2003, "Involvement of the Lateral Hypothalamic Peptide Orexin in Morphine Dependence and Withdrawal," J. Neurosci., 23(8):3106-3111.
Hamlin et al., 2007, "The Neural Correlates and Role of D1 Dopamine Receptors in Renewal of Extinguished Alcohol-Seeking," Neuroscience 146:525-536.
Hara et al., 2001, "Genetic Ablation of Orexin Neurons in Mice Results in Narcolepsy, Hypophagia, and Obesity," Neuron, 30:345-354.
International Search Report mailed Mar. 5, 2013 for International Patent Application No. PCT/EP2012/076447, filed Dec. 20, 2012.
Kane et al., 2000, "Nicotine Up-Regulates Expression of Orexin and Its Receptors in Rat Brain," Endocrinology, 141:3623-3629.
Kane et al., 2001, "Hypothalamic orexin-A binding sites are downregulated by chronic nicotine treatment in the rat," Neuroscience Letters 298:1-4.
Kang et al., 2009, "Amyloid-β Dynamics Are Regulated by Orexin and the Sleep-Wake Cycle," Science, 326:1005-1007.
Kirchgessner et al., 1999, "Orexin Synthesis and Response in the Gut," Neuron, 24:941-951.
Lawrence et al., 2006, "The orexin system regulates alcohol-seeking in rats," British Journal of Pharmacology, 148:752-759.
Lin et al., 1999, "The Sleep Disorder Canine Narcolepsy is Caused by a Mutation in the *Hypocretin (Orexin) Receptor 2* Gene," Cell, 98:365-376.
Malherbe et al., 2009, "Biochemical and Electrophysiological Characterization of Almorexant, a Dual Orexin 1 Receptor ($OX_1$)/Orexin 2 Receptor ($OX_2$) Antagonist: Comparison with Selective $OX_1$ and $OX_2$ Antagonists," Molecular Pharmacology, 76:618-631.
Mignot et al., 2001, "Complex HLA-DR and -DQ Interactions Confer Risk of Narcolepsy-Cataplexy in Three Ethnic Groups," Am. J. Hum. Genet., 68:686-699.
Minot et al., 2001, "Narcolepsy and the HLA System," N. Engl. J. Med., 344:686-693 at p. 692.
Nakamura et al., 2000, "Orexin-induced hyperlocomotion and stereotypy are mediated by the dopaminergic system," Brain Research 873:181-187.
Peyron et al., 1998, "Neurons Containing Hypocretin (Orexin) Project to Multiple Neuronal Systems," Journal of Neuroscience, 18(23):9996-10015.
Peyron et al., 2000, "A mutation in a case of early onset narcolepsy and a generalized absence of hypocretin peptides in human narcoleptic brains," Nature Medicine, 6:991-997.
Piper et al., 2000, "The novel brain neuropeptide, orexin-A, modulates the sleep-wake cycle of rats," European Journal of Neuroscience, 12:726-730.
Richards et al., 2008, "Inhibition of orexin-1/hypocretin-1 receptors inhibits yohimbine-induced reinstatement of ethanol and sucrose seeking in long-evans rats," Psychopharmacology, 199:109-117.
Sakurai et al., 1998, "Orexins and Orexin Receptors: A Family of Hypothalamic Neuropeptides and G Protein-Coupled Receptors That Regulate Feeding Behavior," Cell, 92:573-585.
Sakurai, 1999, "Orexins and orexin receptors: implication in feeding behavior," Regulatory Peptides, 85:25-30.
Sakurai, 2007, "The neural circuit of orexin (hypocretin): maintaining sleep and wakefulness," Nature Reviews Neuroscience, 8:171-181.
Samson et al., 1999, "Cardiovascular regulatory actions of the hypocretins in brain," Brain Research, 831:248-253.
Schneider et al., 2007, "Orexigenic Peptides and Alcohol Intake: Differential Effects of Orexin, Galanin, and Ghrelin," Alcoholism: Clinical and Experimental Research, 31:1-8.
Shirasaka et al., 1999, "Sympathetic and cardiovascular actions of orexins in conscious rats," Am. J. Physiol. 277 (Regulatory Integrative Comp. Physiol. 46): R1780-R1785.
Takahashi et al., 1999, "Stimulation of Gastric Acid Secretion by Centrally Administered Orexin-A in Conscious Rats," Biochemical and Biophysical Research Communications, 254:623-627.
Van Den Pol, 1999, "Hypothalamic Hypocretin (Orexin): Robust Innervation of the Spinal Cord," Journal of Neuroscience, 19:3171-3182.
Winrow et al., 2010, "Orexin receptor antagonism prevents transcriptional and behavioral plasticity resulting from stimulant exposure," Neuropharmacology, 58:185-194.
Written Opinion of the International Searching Authority mailed May 3, 2013 for International Patent Application No. PCT/EP2012/076447, filed Dec. 20, 2012.
Yamanaka et al., 2002, "Orexins Activate Histaminergic Neurons via the Orexin 2 Receptor," Biochemical and Biophysical Research Communications, 290:1237-1245.

* cited by examiner

2-AZABICYCLO[4.1.0]HEPTANE DERIVATIVES AS OREXIN RECEPTOR ANTAGONISTS FOR THE TREATMENT OF CERTAIN DISORDERS

This application is a national stage application of International Application No. PCT/EP2013/055548, filed Mar. 18, 2013, which claims the benefit of Italian Patent Application No. MI2012A000424, filed Mar. 19, 2012, each of which is incorporated herein by reference in its entirety.

FIELD OF THE INVENTION

The invention relates to novel 2-azabicyclo[4.1.0]heptane derivatives and their use as pharmaceuticals. The invention also concerns a process for the preparation of those compounds, pharmaceutical compositions containing one or more compounds of formula (I) and their use as dual antagonists of the Orexin 1 and Orexin 2 receptors.

BACKGROUND OF THE INVENTION

Orexin (or hypocretin) signaling is mediated by two receptors and two peptide agonists. The two orexin peptides (orexin A and orexin B) herein after referred to as orexins, bind to two high affinity receptors, termed Orexin-1 and Orexin-2 receptors. The Orexin-1 receptor is selective in favour of orexin A, while the Orexin-2 receptor binds both orexins with similar affinities. The orexins, are cleavage products of the same gene, prepro-orexin. In the central nervous system neurons expressing prepro-orexin, the precursor from which orexin is produced, are found in the perifornical nucleus, the dorsal hypothalamus and the lateral hypothalamus (C. Peyron et al., J. Neurosci., 1998, 18(23), 9996-10015). Orexinergic cells in these nuclei project to many areas of the brain, extending rostrally to the olfactory bulbs and caudally to the spinal cord (van den Pol, A. N. et al., J. Neuroscience., 1999, 19(8), 3171-3182).

The broad CNS distribution of orexin projections and neurons expressing orexin receptors is suggestive of orexin involvement in a number of physiological functions including; feeding, drinking, arousal, stress, reward, metabolism and reproduction (T. Sakurai, Nature Reviews Neuroscience, 2007, 8(3), 171-181). The targeted necrosis of cells expressing prepro-orexin suggests the most physiologically important roles of the orexins are likely to be effects on arousal, feeding and metabolism (J. Hara et al., Neuron, 2001, 30, 345-354). A prominent orexin neuronal projection via the vagus nerve probably mediates central orexin effects on cardiac parameters (W. K. Samson et al., Brain Res., 1999, 831, 248-253; T. Shirasaka et al., Am. J. Physiol., 1999, 277, R1780-R1785; C.-T. Chen et al., Am. J. Physiol., 2000, 278, R692-R697), gastric acid secretion and gastric motility (A. L. Kirchgessner and M.-T. Liu, Neuron, 1999, 24, 941-951; N. Takahashi et al., Biochem. Biophys. Res. Commun., 1999, 254, 623-627).

Several lines of evidence indicate that the orexin system is an important modulator of arousal. Rodents administered orexins intracerebroventricularly spend more time awake (Piper et al., J. Neurosci. 2000, 12, 726-730). Orexin mediated effects on arousal have been linked to orexin neuronal projections to histaminergic neurons in the tuberomammillary nucleus (TMN) (Yamanaka et al., Biochem. Biophys. Res. Comm. 2002, 290, 1237-1245). TMN neurons express the orexin-2 receptor primarily, and the orexin-1 receptor to a lesser extent. Rodents whose prepro-orexin gene has been knocked out, or whose orexigenic neurons have been lesioned, display altered sleep/wake cycles similar to narcolepsy (Chemelli et al., Cell 1999, 98, 437-451; Hara et al., 2001, supra). Dog models of narcolepsy have been shown to have mutant or nonfunctional orexin-2 receptors (Lin et al., Cell 1999, 98, 365-376). Human narcolepsy appears to be linked to deficient orexin signalling, likely related to immune ablation of orexinergic neurons in the lateral hypothalamus (Mignot et al., Am. J. Hum. Genet. 2001, 68: 686-699; Minot & Thorsby, New England J. Med. 2001, 344, 692), or, in rare cases, to mutations in the orexin-2 gene (Peyron et al., Nature Med. 2000, 6, 991-997). The disclosure that rats, dogs and humans treated with the dual orexin-1/2 receptor antagonist, ACT-078573 (Brisbare-Roch et al., Nature Medicine, 2007, 13, 150-155) exhibited decreased alertness together with characteristic clinical and EEG (electroencephalographic) signs of sleep provides evidence to support a role for the orexin system in the regulation of arousal, sleep and wake states. EEG data indicates that orexin-2 may be more important than orexin-1 in the modulation of sleep/wake (P. Malherbe et al., Molecular Pharmacology (2009) 76(3):618-31; C. Dugovic et al., J. Pharmacol. Exp. Ther., 2009, 330(1), 142-151). Disorders of the sleep-wake cycle are therefore likely targets for orexin-2 receptor antagonist therapy. Examples of such disorders include sleep-wake transition disorders, insomnia, restless legs syndrome, jet-lag, disturbed sleep, and sleep disorders secondary to neurological disorders (e.g., manias, depressions, manic depression, schizophrenia, and pain syndromes (e.g., fibromyalgia, neuropathic pain). The orexin system also interacts with brain dopamine systems. Intracerebroventricular injections of orexins in mice increase locomotor activity, grooming and stereotypy; these behavioural effects are reversed by administration of D2 dopamine receptor antagonists (Nakamura et al., Brain Research, 873(1), 181-7). Therefore, orexin-2 modulators may be useful to treat various neurological disorders; e.g., agonists or up-regulators to treat catatonia, antagonists or down-regulators to treat Parkinson's disease, Tourette's syndrome, anxiety, delirium and dementias. Recent evidence indicates a role for orexin in the pathogenesis of Alzheimer disease (Kang et al, Science Express, 2009, 1-10). Brain interstitial fluid levels of amyloid-beta were demonstrated to fluctuate diurnally in both humans and rodents with sleep deprivation in rodents leading to significant increases in brain interstitial fluid levels of amyloid-beta. Infusion of a dual orexin antagonist in rodents suppressed interstitial levels of amyloid-beta and abolished the natural diurnal variation of amyloid-beta. The reduction of interstitial fluid amyloid-beta levels is correlated with reduced amyloid plaque formation, a hallmark of Alzheimer's disease, and consequently the regulation of sleep time could potentially inhibit amyloid-beta aggregation and slow the progression of Alzheimer's disease. Orexin neurons project to many regions of the brain associated with reward function (T. Sakurai, supra) and research, focusing on animal models of drug intake, reward, and reinstatement, has expanded the link between the orexin system and addiction. A comprehensive set of data suggest that drugs of abuse activate the orexin system, which in turn enhances drug reward or drug seeking (G. Aston-Jones et al., Neuropharmacology, 2009, 56 (Suppl 1) 1 12-121. Thus interactions between nicotine (J. K. Kane et al., Endocrinology, 2000, 141 (10), 3623-3629; J. K. Kane et al., Neurosci. Lett, 2001, 298(1), 1-4), morphine (D. Georgescu, et al., J. Neurosci., 2003, 23(8), 3106-3111) and amphetamine (C. J. Winrow et al., Neuropharmacology, 2010, 58(1), 185-94) and the orexin system have been demonstrated. Additional studies from a number of laboratories have demonstrated an important relationship between the Orexin system and ethanol consumption. As examples, ethanol consumption in an alcohol-preferring strain of rat was shown to up regulate Orexin mRNA in the lateral hypothalamus and that an Orexin-1 receptor antagonist reduced operant responding for ethanol (Lawrence, et. al., Br. J. Pharmacol., 2006, 148, 752-759). Treatment with an orexin-1 antagonist has also been shown to decrease operant responding for ethanol (Richards, et. al., Psychopharmacology, 2008, 199 (1), 109-117). Other studies have demonstrated increased Fos activation of orexin neurons following contextual reinstatement to ethanol seeking (Dayas, et. al., Biol. Psychiatry, 2008, 63 (2), 152-157 and Hamlin, et. al., Neuroscience, 2007, 146, 525-536). Studies have also shown increased ethanol consumption following Orexin infusion into the paraventricular nucleus of the hypothalamus or in the lateral hypothalamus (Schneider, et. al., Alcohol. Clin. Exp. Res., 2007, 37(11), 1858-1865). These studies provide evidence that modulation of the Orexin system effects alcohol preference and therefore Orexin receptor antagonists are likely to be useful for the treatment of alcoholism.

Orexins and their receptors have been found in both the myenteric and submucosal plexus of the enteric nervous system, where orexins have been shown to increase motility in vitro (Kirchgessner & Liu, Neuron 1999, 24, 941-951) and to stimulate gastric acid secretion in vitro (Takahashi et al., Biochem. Biophys. Res. Comm. 1999, 254, 623-627). Orexin mediated effects on the gut may be driven by a projection via the vagus nerve (van den Pol, 1999, supra), as vagotomy or atropine prevent the effect of an intracerebroventricular injection of orexin on gastric acid secretion (Takahashi et al., 1999, supra). Orexin receptor antagonists or other down-regulators of orexin receptor-mediated systems are therefore potential treatments for ulcers, irritable bowel syndrome, diarrhea and gastroesophageal reflux. Body weight may also be affected by orexin-mediated regulation of appetite and metabolism (T. Sakurai et al., Cell, 1998, 92(4), 573-585; T. Sakurai, Reg. Pept, 1999, 85(1), 25-30). Some effects of orexin on metabolism and appetite may be mediated in the gut, where, as mentioned, orexins alter gastric motility and gastric acid secretion. Orexin receptor antagonists therefore are likely to be useful in treatment of overweight or obesity and conditions related to overweight or obesity, such as insulin resistance, type II diabetes, hyperlipidemia, gallstones, angina, hypertension, breathlessness, tachycardia, infertility, sleep apnea, back and joint pain, varicose veins and osteoarthritis. Conversely, orexin receptor agonists are likely to be useful in treatment of underweight and related conditions such as hypotension, bradycardia, amenorrhea and related infertility, and eating disorders such as anorexia and bulimia. Intracerebroventricularly administered orexins have been shown to increase mean arterial pressure and heart rate in freely moving (awake) animals (Samson et al., Brain Res. 1999, 831, 248-253; Shirasaka et al., Am. J. Physiol. 1999, 277, R1780-R1785) and in urethane-anesthetized animals (Chen et al., Am. J. Physiol. 2000, 278, R692-R697), with similar results.

Orexin receptor agonists may therefore be candidates for treatment of hypotension, bradycardia and heart failure related thereto, while orexin receptor antagonists may be useful for treatment of hypertension, tachycardia and other arrhythmias, angina pectoris and acute heart failure.

From the foregoing discussion, it can be seen that the identification of orexin receptor antagonists, in one embodiment modulators of the orexin-2 receptor, will be of great advantage in the development of therapeutic agents for the treatment of a wide variety of disorders that are mediated through these receptor systems.

Certain orexin antagonists are disclosed in PCT patent applications: WO2010/0480116, WO2010/051238, WO2006/127550, WO2010/060470, WO2010/060471, WO2003/051368, WO2011/076747 and WO2009/016564. There remains a need, however, for potent orexin dual receptor antagonists with desirable pharmaceutical properties The object of the present invention is to provide 2-azabicyclo[4.1.0]heptane compounds with dual antagonist activity at the Orexin 1 and Orexin 2 receptors.

SUMMARY OF THE INVENTION

The present invention provides a compound of formula (I) or a pharmaceutically acceptable salt thereof:

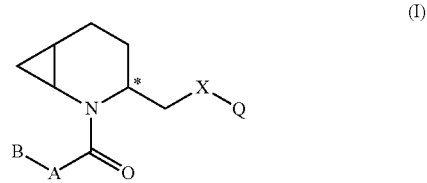

wherein
X is NH, or O;
Q is 5-6 membered heteroaryl group, which may be substituted by one or more substituents independently selected from a group consisting of: C1-C4 alkyl, halogen, halo C1-C4 alkyl, C1-C4 alkoxy, CN;
A is phenyl or a 5-6 heteroaryl group, which may be substituted by one or more substituents independently selected from a group consisting of: C1-C4 alkyl, halogen, halo C1-C4 alkyl, C1-C4 alkoxy, CN;
B may assume different meanings from A and is phenyl or a 5-6 membered heteroaryl group, which may be substituted by one or more substituents independently selected from a group consisting of: C1-C4 alkyl, halogen, halo C1-C4 alkyl, C1-C4 alkoxy, CN.

Compounds of formula (I) are provided as (S) enantiomers at the chiral carbon represented with an asterisk (*). It is intended in the context of the present invention that stereochemical isomers enriched in configuration (S) of formula (I) correspond in one embodiment to at least 90% e.e. In another embodiment the isomers correspond to at least 95% e.e. In another embodiment the -isomers correspond to at least 99% e.e.

This invention includes in its scope of protection all the possible isomers and racemic mixtures. Wherever should be present further symmetry centres, this invention includes all the possible diastereoisomers and relative mixtures as well.

In a first embodiment, the present invention provides a compound of formula (II), corresponding to a compound of formula (I) in which

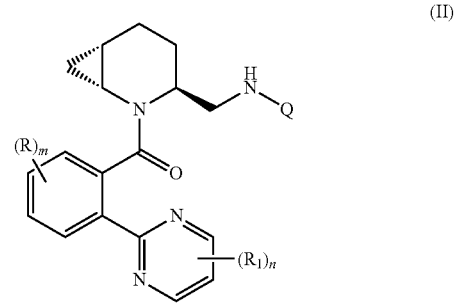

X is N—H, A is a phenyl derivative, B is a pyrimidinyl derivative and R and $R_1$ are independently selected from a group consisting of: C1-C4 alkyl, halogen, halo C1-C4 alkyl, C1-C4 alkoxy, CN; m is 0, 1, 2, 3 or 4; n is 1, 2, or 3.

In another aspect the invention concerns pharmaceutical compositions comprising a compound of formula (I) and a pharmaceutically acceptable carrier.

In another aspect the invention concerns a compound of Formula (I) as medicament; in particular it concerns its use for the manufacturing of a medicament for the treatment of pathologies where an antagonist of the OX1/OX2 antagonist is needed, such as the treatment of obesity, sleep disorders, compulsive disorders, drug dependency and schizophrenia.

DETAILED DESCRIPTION OF THE INVENTION

The present invention thus provides a compound of formula (I) or a pharmaceutically acceptable salt thereof:

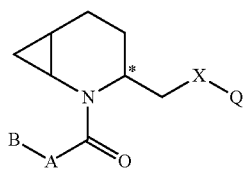

(I)

wherein
X is NH, or O;
Q is 5-6 membered heteroaryl group, which may be substituted by one or more substituents independently selected from a group consisting of: C1-C4 alkyl, halogen, halo C1-C4 alkyl, C1-C4 alkoxy, CN;
A is phenyl or a 5-6 heteroaryl group, which may be substituted by one or more substituents independently selected from a group consisting of: C1-C4 alkyl, halogen, halo C1-C4 alkyl, C1-C4 alkoxy, CN;
B may assume different meanings from A and is phenyl or a 5-6 membered heteroaryl group, which may be substituted by one or more substituents independently selected from a group consisting of: C1-C4 alkyl, halogen, halo C1-C4 alkyl, C1-C4 alkoxy, CN.

The term "5- or 6-membered heteroaryl ring" refers to a monocyclic 5- or 6-membered heterocyclic group containing 1 to 3 heteroatoms and having at least one heteroatom selected from nitrogen, oxygen and sulfur, and containing at least 1 carbon atom. Examples of 5 and 6-membered heteroaryl groups include pyrrolyl, imidazolyl, pyrazolyl, oxazolyl, isoxazolyl, oxadiazolyl, isothiazolyl, thiazolyl, furyl, thienyl, thiadiazolyl, pyridyl, triazolyl, triazinyl, pyridazinyl, pyrimidinyl and pyrazinyl.

The term "C1-C4 alkyl" refers to an alkyl group having from one to four carbon atoms, in all isomeric forms, such as methyl, ethyl, propyl, isopropyl, butyl, isobutyl, sec-butyl and tert-butyl. The term "n-C1-C4 alkyl" refers to the unbranched alkyls as defined above.

The term "C1-C4 alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term "halogen" and its abbreviation "halo" refers to fluorine (F), chlorine (Cl), bromine (Br) or iodine (I). Where the term "halo" is used before another group, it indicates that the group is substituted by one, two or three halogen atoms. For example, "halo$C_{1-4}$alkyl" refers to groups such as trifluoromethyl, bromoethyl, trifluoropropyl, and other groups derived from $C_{1-4}$alkyl groups as defined above; and the term "halo$C_{1-4}$alkoxy" refers to groups such as trifluoromethoxy, bromoethoxy, trifluoropropoxy, and other groups derived from $C_{1-4}$alkoxy groups as defined above.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

Pharmaceutical acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Hereinafter, compounds of formula (I) and their pharmaceutically acceptable salts, and solvates defined in any aspect of the invention (except intermediate compounds in chemical processes) are referred to as "compounds of the invention".

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula (I) and following of this invention can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers and mixtures thereof. Certain of the substituted heteroaromatic groups included in compounds of formula (I) may exist in one or more tautomeric forms. The present invention includes within its scope all such tautomeric forms, including mixtures.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertible in the mammalian (e.g. human) body to the inventive compounds are however included.

In a first embodiment, the present invention provides a compound of formula (II), corresponding to a compound of formula (I) in which

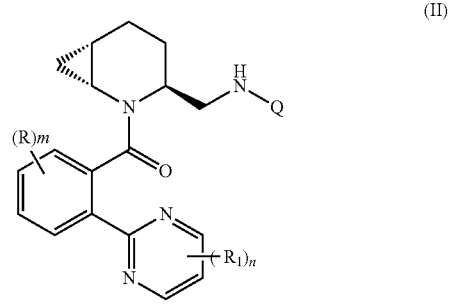

(II)

X is N—H, A is a phenyl derivative, B is a pyrimidinyl derivative and R and $R_1$ are independently selected from a group consisting of: C1-C4 alkyl, halogen, halo C1-C4 alkyl, C1-C4 alkoxy, CN; m is 0, 1, 2, 3 or 4; n is 1, 2, or 3.

In a second embodiment, the present invention provides a compound of formula (III), corresponding to a compound of formula (I) in which

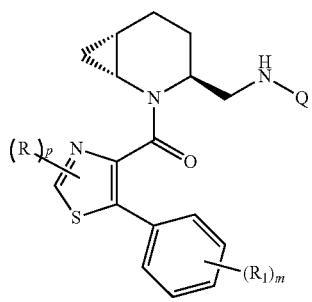

(III)

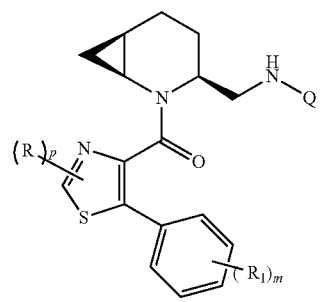

(VI)

X is N—H, A is a thiazolyl derivative, B is a phenyl derivative and X is N—H, A is a phenyl derivative, B is a pyrimidinyl derivative and R and $R_1$ are independently selected from a group consisting of: C1-C4 alkyl, halogen, halo C1-C4 alkyl, C1-C4 alkoxy, CN; m is 0, 1, 2, 3 or 4; p is 0 or 1.

In a third embodiment, the present invention provides a compound of formula (IV), corresponding to a compound of formula (I) in which

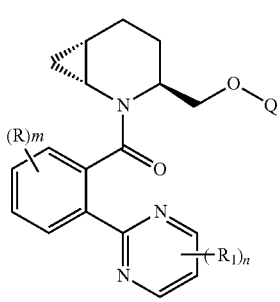

(IV)

X is O, A is a phenyl derivative, B is a pyrimidinyl derivative and R and $R_1$ are independently selected from a group consisting of: C1-C4 alkyl, halogen, halo C1-C4 alkyl, C1-C4 alkoxy, CN; m is 0, 1, 2, 3 or 4; n is 1, 2, or 3.

In a fourth embodiment, the present invention provides a compound of formula (V), corresponding to a compound of formula (I) in which

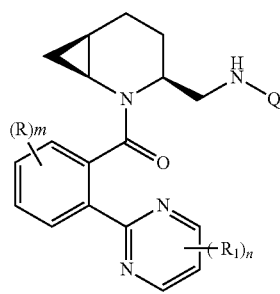

(V)

X is N—H, A is a phenyl derivative, B is a pyrimidinyl derivative and R and $R_1$ are independently selected from a group consisting of: C1-C4 alkyl, halogen, halo C1-C4 alkyl, C1-C4 alkoxy, CN; m is 0, 1, 2, 3 or 4; n is 1, 2, or 3.

In a fifth embodiment, the present invention provides a compound of formula (VI), corresponding to a compound of formula (I) in which X is N—H, A is a thiazolyl derivative, B is a phenyl derivative and R and $R_1$ are independently selected from a group consisting of: C1-C4 alkyl, halogen, halo C1-C4 alkyl, C1-C4 alkoxy, CN; m is 0, 1, 2, 3 or 4; p is 0 or 1.

Example compounds of the invention include:
(5-chloro-2-(pyrimidin-2-yl)phenyl)((1R,3S,6S)-3-(((4-(trifluoromethyl)pyridin-2-yl)amino-) methyl)-2-azabicyclo[4.1.0]heptan-2-yl)methanone;
4-(pyrimidin-2-yl)-3-((1R,3S,6S)-3-(((5-(trifluoromethyl)pyridin-2-yl)amino)methyl)-2-azabicyclo[4.1.0]heptane-2-carbonyl)benzonitrile;
((1R,3S,6S)-3-(((5-chloropyridin-2-yl)amino)methyl)-2-azabicyclo[4.1.0]heptan-2-yl)(5-methyl-2-(pyrimidin-2-yl)phenyl)methanone;
(5-methyl-2-(pyrimidin-2-yl)phenyl)((1R,3S,6S)-3-(((5-(trifluoromethyl)pyridin-2-yl)amino)-methyl)-2-azabicyclo[4.1.0]heptan-2-yl)methanone;
(5-chloro-2-(pyrimidin-2-yl)phenyl)((1R,3S,6S)-3-(((5-(trifluoromethyl)pyridin-2-yl)amino)-methyl)-2-azabicyclo[4.1.0]heptan-2-yl)methanone;
(5-chloro-2-(pyrimidin-2-yl)phenyl)((1R,3S,6S)-3-(((5-chloropyridin-2-yl)amino)methyl)-2-azabicyclo[4.1.0]heptan-2-yl)methanone;
(5-chloro-2-(pyrimidin-2-yl)phenyl)((1R,3S,6S)-3-(((4-(trifluoromethyl)pyridin-2-yl)amino)-methyl)-2-azabicyclo[4.1.0]heptan-2-yl)methanone;
4-(pyrimidin-2-yl)-3-((1R,3S,6S)-3-(((4-(trifluoromethyl)pyridin-2-yl)amino)methyl)-2-azabicyclo[4.1.0]heptane-2-carbonyl)benzonitrile;
3-((1R,3S,6S)-3-(((5-chloropyridin-2-yl)amino)methyl)-2-azabicyclo[4.1.0]heptane-2-carbonyl)-4-(pyrimidin-2-yl)benzonitrile;
4-(pyrimidin-2-yl)-3-((1R,3S,6S)-3-(((4-(trifluoromethyl)pyrimidin-2-yl)amino)methyl)-2-azabicyclo[4.1.0]heptane-2-carbonyl)benzonitrile;
(5-methyl-2-(pyrimidin-2-yl)phenyl)((1R,3S,6S)-3-(((4-(trifluoromethyl)pyrimidin-2-yl)amino)-methyl)-2-azabicyclo[4.1.0]heptan-2-yl)methanone;
(2-methyl-5-phenylthiazol-4-yl)((1R,3S,6S)-3-(((5-(trifluoromethyl)pyridin-2-yl)amino)methyl)-2-azabicyclo[4.1.0]heptan-2-yl)methanone;
((1R,3S,6S)-3-(((5-chloropyridin-2-yl)amino)methyl)-2-azabicyclo[4.1.0]heptan-2-yl)(2-methyl-5-phenylthiazol-4-yl)methanone;
(2-methyl-5-phenylthiazol-4-yl)((1R,3S,6S)-3-(((4-(trifluoromethyl)pyrimidin-2-yl)amino)-methyl)-2-azabicyclo[4.1.0]heptan-2-yl)methanone;
3-((1R,3S,6S)-3-(((5-chloropyridin-2-yl)oxy)methyl)-2-azabicyclo[4.1.0]heptane-2-carbonyl)-4-(pyrimidin-2-yl)benzonitrile;
3-((1R,3S,6S)-3-(((5-fluoropyridin-2-yl)oxy)methyl)-2-azabicyclo[4.1.0]heptane-2-carbonyl)-4-(pyrimidin-2-yl)benzonitrile;

- (5-chloro-2-(pyrimidin-2-yl)phenyl)((1R,3S,6S)-3-(((5-fluoropyridin-2-yl)oxy)methyl)-2-azabicyclo[4.1.0]heptan-2-yl)methanone;
- (5-chloro-2-(pyrimidin-2-yl)phenyl)((1R,3S,6S)-3-(((5-(trifluoromethyl)pyridin-2-yl)oxy)methyl)-2-azabicyclo[4.1.0]heptan-2-yl)methanone;
- (5-chloro-2-(pyrimidin-2-yl)phenyl)((1R,3S,6S)-3-(((5-chloropyridin-2-yl)oxy)methyl)-2-azabicyclo[4.1.0]heptan-2-yl)methanone;
- ((1R,3S,6S)-3-(((5-chloropyridin-2-yl)oxy)methyl)-2-azabicyclo[4.1.0]heptan-2-yl)(5-methyl-2-(pyrimidin-2-yl)phenyl)methanone;
- (5-methyl-2-(pyrimidin-2-yl)phenyl)((1R,3S,6S)-3-(((5-(trifluoromethyl)pyridin-2-yl)oxy)-methyl)-2-azabicyclo[4.1.0]heptan-2-yl)methanone;
- (5-methyl-2-(pyrimidin-2-yl)phenyl)((1S,3S,6R)-3-(((5-(trifluoromethyl)pyridin-2-yl)amino)-methyl)-2-azabicyclo[4.1.0]heptan-2-yl)methanone;
- (5-chloro-2-(pyrimidin-2-yl)phenyl)((1S,3S,6R)-3-(((5-(trifluoromethyl)pyridin-2-yl)amino)-methyl)-2-azabicyclo[4.1.0]heptan-2-yl)methanone;
- 4-(pyrimidin-2-yl)-3-((1S,3S,6R)-3-(((5-(trifluoromethyl)pyridin-2-yl)amino)methyl)-2-azabicyclo[4.1.0]heptane-2-carbonyl)benzonitrile;
- (5-chloro-2-(pyrimidin-2-yl)phenyl)((1S,3S,6R)-3-(((4-(trifluoromethyl)pyridin-2-yl)amino)-methyl)-2-azabicyclo[4.1.0]heptan-2-yl)methanone;
- (5-chloro-2-(pyrimidin-2-yl)phenyl)((1S,3S,6R)-3-(((5-chloropyridin-2-yl)amino)methyl)-2-azabicyclo[4.1.0]heptan-2-yl)methanone;
- (5-methyl-2-(pyrimidin-2-yl)phenyl)((1S,3S,6R)-3-(((4-(trifluoromethyl)pyridin-2-yl)amino)-methyl)-2-azabicyclo[4.1.0]heptan-2-yl)methanone;
- ((1S,3S,6R)-3-(((5-chloropyridin-2-yl)amino)methyl)-2-azabicyclo[4.1.0]heptan-2-yl)(5-methyl-2-(pyrimidin-2-yl)phenyl)methanone;
- (5-chloro-2-(pyrimidin-2-yl)phenyl)((1S,3S,6R)-3-(((4-(trifluoromethyl)pyrimidin-2-yl)amino)-methyl)-2-azabicyclo[4.1.0]heptan-2-yl)methanone;
- (5-methyl-2-(pyrimidin-2-yl)phenyl)((1S,3S,6R)-3-(((4-(trifluoromethyl)pyrimidin-2-yl)amino)-methyl)-2-azabicyclo[4.1.0]heptan-2-yl)methanone;
- (2-methyl-5-phenylthiazol-4-yl)((1S,3S,6R)-3-(((5-(trifluoromethyl)pyridin-2-yl)amino)methyl)-2-azabicyclo[4.1.0]heptan-2-yl)methanone; or their pharmaceutically acceptable salts thereof.

A further aspect of this invention concerns a process for the preparation of a compound of formula (I) comprising the following steps represented in the scheme below:

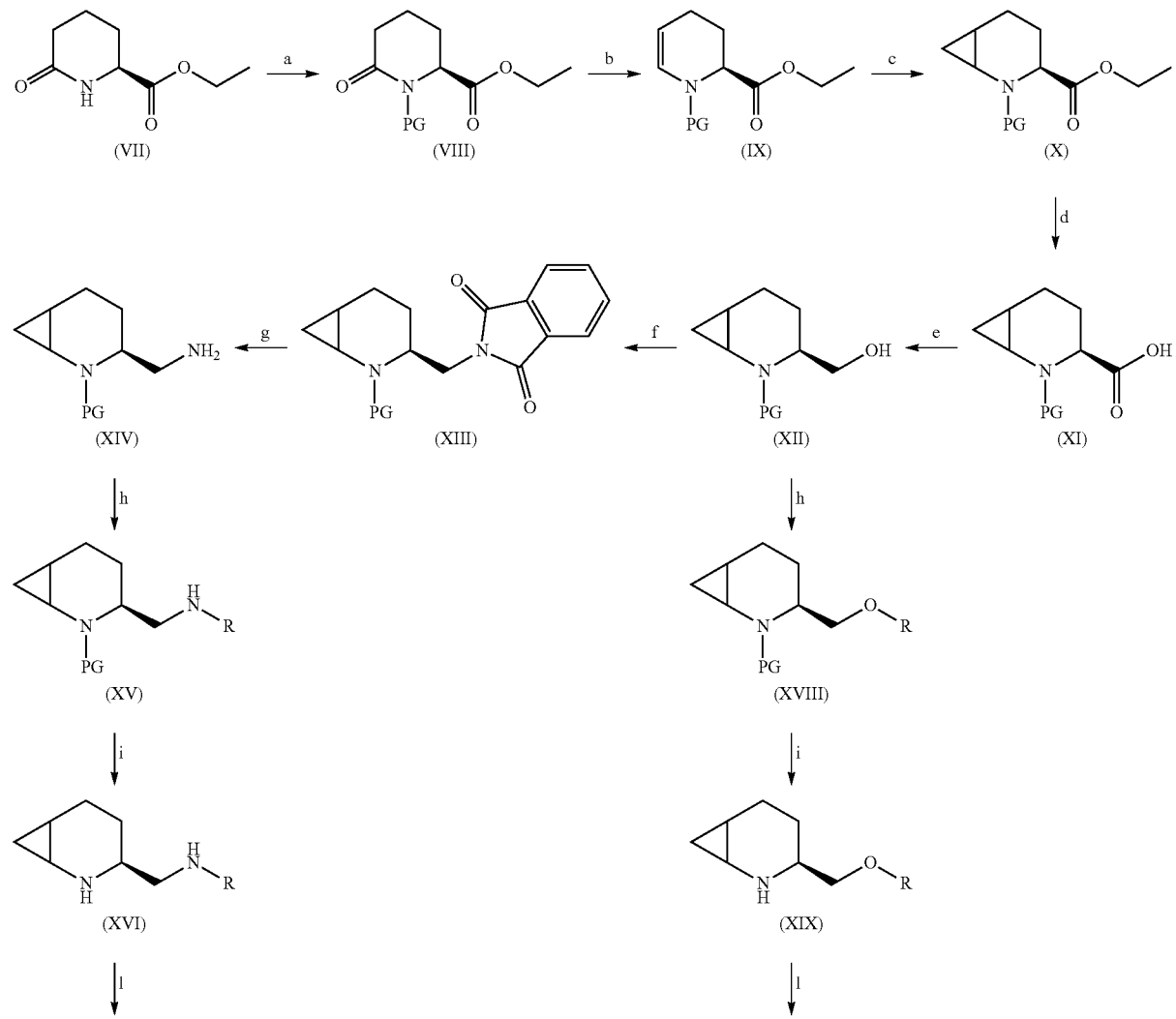

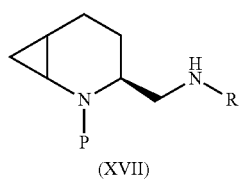

(XVII)

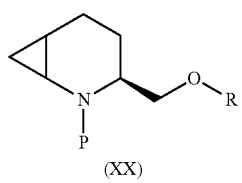

(XX)

Step a) means introducing a protecting group, such as BOC, to obtain a compound of formula (VIII);
Step b) means reducing with suitable reducing agent, such as LiEt$_3$BH, to obtain a compound of formula (IX)
Step c) means reacting a compound of formula (IX) with suitable reagents, such as CH$_2$I$_2$ and Et$_2$Zn, to obtain a compound of formula (X);
Step d) means hydrolysis of a compound of formula (X) to obtain a compound of formula (XI);
Step e) means reducing with an appropriate reagent, such as BH$_3$, to obtain a compound of formula (XII);
Step f) means converting the alcohol with an amine by using a precursor, such as phtalimide, under Mitsunobu conditions to obtain a compound of formula (XIII);
Step g) means deprotection of the phtalimide by using a suitable reagent, such as hydrazine, to obtain a compound of formula (XIV);
Step h) means adding a compound of formula R—X, where R is defined as above and X is a leaving group, to the compounds of formula (XIV) or (XII) to obtain compounds (XV) and (XVIII) respectively;
Step i) means cleaving the protecting group (PG), such as the BOC group from the compounds of formula (XV) and (XVIII) to obtain compounds of Formula (XVI) and (XIX) respectively;
Step I) means reacting a compound of Formula (XVI) and (XIX) with RCOOH or a reactive derivative thereof (such as anhydride or acyl chloride) in the presence of coupling reagents in the presence of a base, where P is defined as above.

In the commercially available compound of formula (VII), the absolute stereochemistry of the carbon represented with (*) is (S). As a consequence, the stereochemistry of products of formula (I) to (VI) has been reasonably assigned on the assumption that the absolute configuration at this centre is retained.

During step c) two diastereoisomers are formed: they are indicated as "trans" (product Xa) and "cis" (product Xb) relatively to the stereochemistry of carbon represented with (*).

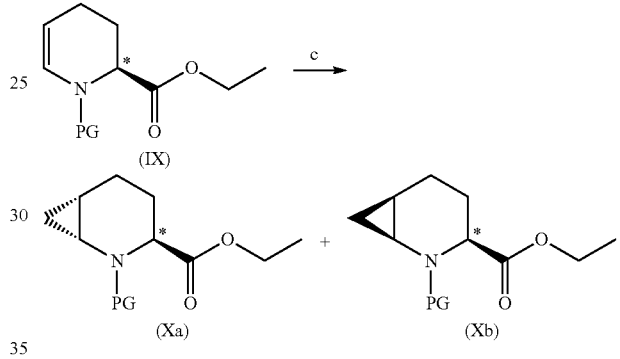

When the hydrolysis (step d) was conducted at room temperature the "trans" derivative (XIa) was predominantly obtained; when the hydrolysis was performed at higher temperature both "cis" and "trans" diastereoisomers (XIb and XIa respectively) were obtained.

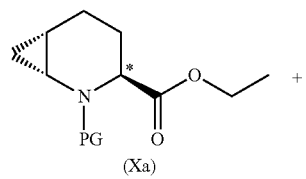

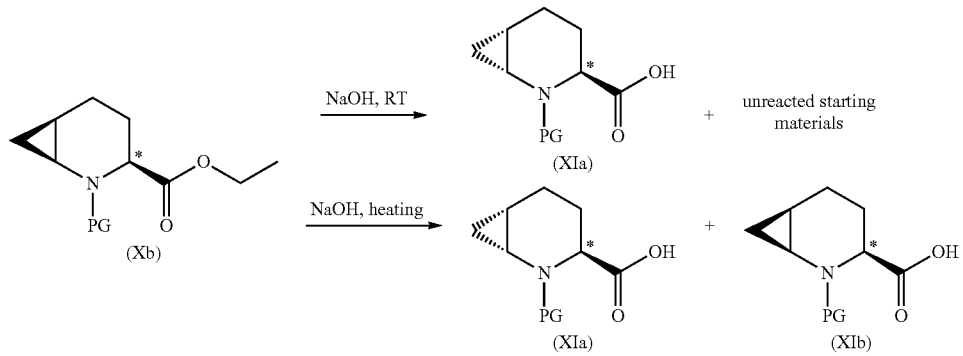

"Leaving group" is as understood by a skilled chemist, i.e. a group which can be displaced by a nucleophile in e.g. a $S_N2$, $S_N1$ or $S_NAr$ type reaction, such as an halogen or a reactive residue of a alkyl/aryl sulphonic acid, for example mesylate, tosylate, triflate.

The compounds of formula (I) or their pharmaceutically acceptable salts can be used as medicaments, in particular as antagonists of the Orexin 1/Orexin 2 receptors.

They could be used in combination with a pharmaceutically acceptable carrier and, optionally, with suitable excipients, to obtain pharmaceutical compositions. The term "pharmaceutically acceptable carrier" means solvents, carrier agents, diluting agents and the like which are used in the administration of compounds of the invention.

Such pharmaceutical compositions can be administered by parenteral, oral, buccal, sublingual, nasal, rectal and topical or transdermal administration.

Compositions of this invention suitable for the oral administration will be conveniently discrete units such as tablets, capsules, cachet, powders or pellets, or as liquid suspension. The tablets can contain also suitable excipients routinely used in pharmaceutical field such as pre-gelatinised starch, microcrystalline cellulose, sodium glycolate starch, talc, lactose, magnesium stearate, sucrose, stearic acid and mannitol.

Compositions for parenteral administration conveniently include sterile preparations. Compositions for topical administration may conveniently be formulated as creams, pastes, oils, ointments, emulsions, foams, gels, drops, spray solutions and transdermal patches.

The production of the pharmaceutical compositions can be effected in a manner which will be familiar to any person skilled in the art (see for example Remington, The Science and Practice of Pharmacy, 21 st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically effective amount of a compound of formula (I).

In treatment methods according to the invention, an effective amount of a pharmaceutical composition according to the invention is administered to a subject suffering from or diagnosed as having such disease, disorder or condition.

An "effective amount" means an amount or dose sufficient to generally bring about the desired therapeutic or prophylactic benefit in patients in need of such treatment for the designated disease, disorder or condition. Effective amounts or doses of the compounds of the present invention may be ascertained by routine methods such as modelling, dose escalation studies or clinical trials, and by taking into consideration routine factors, e.g., the mode or route of administration or drug delivery, the pharmacokinetics of the compound, the severity and course of the disease, disorder, or condition, the subject's previous or on-going therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

For avoidance of any doubt, if compounds are described as useful for the prevention or treatment of certain diseases, such compounds are likewise suitable for use in the preparation of a medicament for the prevention or treatment of said diseases.

The compounds according to formula (I) are useful for the prevention or treatment of diseases related to the orexin system.

Such diseases related to the orexin system may be selected from the group consisting of all types of sleep disorders, of stress-related syndromes, of addictions (especially psychoactive substance use, abuse, seeking and reinstatement), of cognitive dysfunctions in the healthy population and in psychiatric and neurologic disorders, of eating or drinking disorders.

In a sub-embodiment, such diseases related to the orexin system may be selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders (notably all types of insomnias, especially primary insomnia).

In another sub-embodiment, such diseases related to the orexin system may be selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another sub-embodiment, such diseases related to the orexin system may be selected from the group consisting of eating disorders that comprise metabolic dysfunction; dysregulated appetite control; compulsive obesities; emeto-bulimia or anorexia nervosa.

In another sub-embodiment, such diseases related to the orexin system may be selected from the group consisting of all types of addictions (especially psychoactive substance use, abuse, seeking and reinstatement) that comprise all types of psychological or physical addictions and their related tolerance and dependence components.

Eating disorders may be defined as comprising metabolic dysfunction; dysregulated appetite control; compulsive obesities; emeto-bulimia or anorexia nervosa.

Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake.

Sleep disorders include all types of parasomnias, insomnias, narcolepsy and other disorders of excessive sleepiness, sleep-related dystonias; restless leg syndrome; sleep apneas;

jet-lag syndrome; shift-work syndrome, delayed or advanced sleep phase syndrome or insomnias related to psychiatric disorders.

Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance.

Addictions may be defined as addiction to one or more rewarding stimuli, notably to one rewarding stimulus. Such rewarding stimuli may be of either natural or synthetic origin. Psychoactive substance use, abuse, seeking and reinstatement are defined as all types of psychological or physical addictions and their related tolerance and dependence components.

Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

Besides, any characteristics described in this invention for the compounds of formula (I) (whether for the compounds themselves, salts thereof, compositions containing the compounds or salts thereof, uses of the compounds or salts thereof, etc.) apply mutatis mutandis to compounds of formula (II), (III), (IV), (V) and (VI).

EXPERIMENTAL SECTION

The invention will be now detailed by means of the following examples relating to the preparation of some invention compounds and to the evaluation of their activity against OX1 receptor and OX2 receptor.

In the procedure that follows, after the starting materials, reference to a description is typically provided. The starting material may not necessarily have been prepared from the description referred to. The Examples' stereochemistry has been assigned on the assumption that the absolute configuration centers are retained.

Reagents used in the following examples were commercially available from various suppliers (for example Sigma-Aldrich, Acros or Apollo scientific) and used without further purifications. Solvents were used in dry form. Reactions in anhydrous environment were run under a positive pressure of dry $N_2$.

Microwave reactions were run on a Biotage Initiator 2.5 instrument.

Proton Nuclear Magnetic Resonance ($^1$H NMR) spectra were recorded on Bruker Avance 400 MHz instrument. Chemical shifts are reported in ppm (δ) using the residual solvent line as internal standard. Splitting patterns are designated as: s, singlet; d, doublet; t, triplet; q, quartet; m, multiplet; b, broad signal.

Mass spectra (MS) were run on a Ion Trap Thermo LCQ classic spectrometer, operating in positive ES(+) and negative ES(−) ionization mode.

UPLC spectra were performed on a Waters Acquity UPLC-SQD instrument using an Acquity UPLC-BEH C18 column (1.7 μM, 50×2.1 mm).

Flash silica gel chromatography was performed on Biotage automatic flash chromatography systems (Sp1 and Isolera systems) using Biotage SNAP HP silica cartridges or Biotage SNAP KP-NH cartridges.

Purifications of some basic compounds were performed using Phenomenex Strata SCX cartridges (55 μm, 70 A).

Thin layer chromatography was carried out using Merck TLC plates Kieselgel 60F-254, visualized with UV light, aqueous permanganate solution, iodine vapours.

The following abbreviations are used herein: DEAD: diethylazodicarboxylate; DIPEA: N,N-diisopropylethylamine; Boc: terbutyloxycarbonyl; DCM: dichloromethane; TFA: trifluoroacetic acid; DMF: dimethylformamide; THF: tetrahydrofuran; RT: room temperature; DMAP: dimethylamino pyridine; AcOEt: ethyl acetate.

Description 1:
(S)-ethyl-6-oxopiperidine-2-carboxylate (D1)

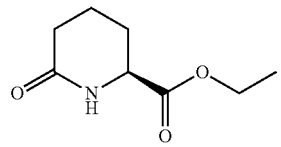

Absolute ethanol (300 mL) was cooled at −5° C. then thionyl chloride (14.01 mL, 192.1 mmol) was added keeping the temperature below 0° C., followed by portionwise addiction of (S)-6-oxopiperidine-2-carboxylic acid (25.0 g, 174.6 mmol). The mixture was stirred at room temperature for 6 hours. The solvent was evaporated, then toluene (300 mL) and $Et_3N$ (48.7 mL) were added. After 0.5 hour the precipitate was filtered and washed with toluene and $Et_2O$. The filtrate was evaporated and the residue treated with $Et_2O$. The precipitate was eliminated and the solution was concentrated to give the title compound as yellow oil. Yield (29.9 g, 100%).

$^1$H NMR (400 MHz, $CDCl_3$): δ 1.30 (t, 3H), 1.75-1.95 (m, 3H), 2.15-2.25 (m, 1H), 2.30-2.45 (m, 2H), 4.08 (m, 1H), 4.24 (q, 2H), 6.43 (br s, 1H).

Description 2: (S)-1-tert-butyl-2-ethyl-6-oxopiperidine-1,2-dicarboxylate (D2)

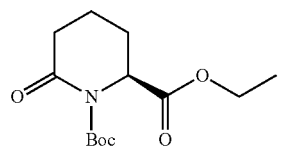 [SMILES: CCOC(=O)[C@@H]1CCCC(=O)N1C(=O)OC(C)(C)C]

To a solution of D1 (29.9 g, 174.6 mmol) in toluene (150 mL), DMAP (1.07 g, 8.73 mmol) was added followed by solution of $Boc_2O$ (45.74 g, 209.6 mmol) in toluene (100 mL). After 3.5 hours additional DMAP (20.0 g, 163.7 mmol) was added and the mixture was stirred at room temperature overnight. An aqueous solution of $NaHCO_3$ (200 mL) was added and the separated organic layer was washed with water, dried over $Na_2SO_4$, filtered and concentrated. The residue was treated with cyclohexane (200 mL) and cooled with an ice bath, the precipitate was eliminated and the solution was concentrated to give a crude mixture which was purified by silica gel column chromatography (cyclohexane/ethyl acetate=6:4) to give the title compound as yellow oil. Yield (41.9 g, 88%).

$^1$H NMR (400 MHz, $CDCl_3$): δ 1.31 (t, 3H), 1.52 (s, 9H), 1.71-1.85 (m, 2H), 2.02-2.11 (m, 1H), 2.16-2.23 (m, 1H), 2.46-2.64 (m, 2H), 4.08 (m, 1H), 4.25 (m, 2H), 4.71 (dd, 1H). ESI+ m/z 565 [2M+Na]+ 294 [M+Na]+

Description 3: (S)-1-tert-butyl-2-ethyl-3,4-dihydropyridine-1,2(2H)-dicarboxylate (D3)

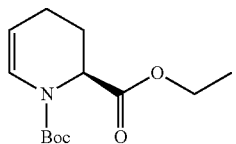 [SMILES: CCOC(=O)[C@@H]1CCC=CN1C(=O)OC(C)(C)C]

To a solution of D2 (20.98 g, 77.32 mmol) in toluene (200 mL) cooled at −50° C., LiEt₃BH 1M in THF (81.2 mL, 81.19 mmol) was added keeping the temperature below −45° C. After 30 minutes at −45° C., DIPEA (57.9 mL, 332.5 mmol) was added followed by DMAP (0.142 g, 1.116 mmol) and trifluoroacetic anhydride (16 mL, 116 mmol). The mixture was stirred at room temperature for 2.5 hours and then cooled at 0° C. Water was added and the separated organic layer was washed with water, dried over Na₂SO₄, filtered and concentrated. The residue was dissolved in DCM (100 mL) and washed with 0.1 M aqueous solution of citric acid (150 mL). The solution was concentrated to give a crude mixture which was purified by silica gel column chromatography (cyclohexane/ethyl acetate=95:5) to give the title compound as orange oil. Yield (15.12 g, 77%).

¹H NMR (400 MHz, CDCl₃): δ 1.27 (m, 3H), 1.45-1.52 (m, 9H), 1.87-2.00 (m, 3H), 2.30-2.39 (m, 1H), 4.15-4.26 (m, 2H), 4.74-4.95 (m, 2H), 6.80-6.90 (m, 1H).

ESI+ m/z 156 [M+H−Boc]+

Description 4: (3S)-2-tert-butyl-3-ethyl-2-azabicyclo[4.1.0]heptane-2,3-dicarboxylate (D4)

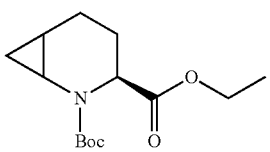 [SMILES: CCOC(=O)[C@@H]1CCC2CC2N1C(=O)OC(C)(C)C]

A solution of D3 (20 g, 78.4 mmol) in toluene (400 mL) was cooled at −30° C., then Et₂Zn 1M in hexanes (235 mL, 235 mmol) and a solution of CH₂I₂ (38 mL, 470 mmol) in toluene (50 mL) were added keeping the temperature below −30° C. The mixture was stirred at −15° C. for 16 hours; the temperature was raised to −5° C. then an aqueous solution of NaHCO₃ was added. The separated organic layer was washed with brine, dried over Na₂SO₄, filtered and concentrated to give the crude mixture of diastereoisomers (28 g).

¹H NMR (400 MHz, CDCl₃): δ 0.22-0.54 (m, 1H), 0.75-0.92 (m, 1H), 1.14-1.32 (m, 4H), 1.45-1.51 (m, 9H), 1.65-2.07 (m, 4H), 2.60-3.03 (m, 1H), 4.12-4.58 (m, 3H).

ESI+ m/z 292 [M+Na]+

Description 5: (1R,3S,6S)-2-(tert-butoxycarbonyl)-2-azabicyclo[4.1.0]heptane-3-carboxylic acid (D5)

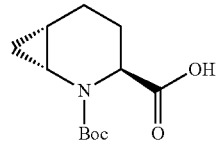 [SMILES: CC(C)(C)OC(=O)N1[C@@H]2C[C@@H]2CC[C@H]1C(=O)O]

To a solution of D4 (25 g, 93 mmol) in ethanol (300 mL) cooled at 0° C., NaOH 2M (93 mL, 186 mmol) was added keeping the temperature below 5° C. The mixture was stirred at 0° C. for 2 hours and at room temperature for 3 hours and half. The solution was concentrated, water and DCM were added and the phases were separated.

The aqueous phase was washed with AcOEt, then i-Pr₂O (the organic phases were collected, washed with water and concentrated to give a residue oil containing the diastereoisomeric mixture of unreacted esters that was used without any other purification in description 6); then the aqueous phase was acidified with acetic acid (pH=4), extracted with AcOEt, dried over Na₂SO₄, filtered and concentrated to give the title compound (D5) as a single diastereoisomer (white solid). Yield (11.0 g, 49%).

¹H NMR (400 MHz, CDCl₃): δ 4.63-4.43 (m, 1H), 2.99-2.90 (m, 1H), 2.10-1.87 (m, 2H), 1.77-1.61 (m, 2H), 1.52 (s, 9H), 1.29-1.19 (m, 1H), 0.94-0.81 (m, 1H), 0.33-0.25 (m, 1H).

Description 6: (3S)-2-(tert-butoxycarbonyl)-2-azabicyclo[4.1.0]heptane-3-carboxylic acid (D6)

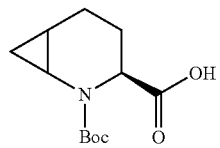 [SMILES: CC(C)(C)OC(=O)N1C2CC2CC[C@H]1C(=O)O]

The oil containing the diastereoisomeric mixture of unreacted esters from description 5 was dissolved in ethanol (300 mL) and NaOH 2M (90 mL, 180 mmol) was added. The mixture was stirred at 50° C. for 24 hours, then the solution was concentrated, water and i-Pr₂O were added and the phases were separated. The aqueous phase was acidified with acetic acid (pH=4), extracted with DCM, dried over Na₂SO₄, filtered and concentrated to obtain the title compound (D6) as diastereoisomeric mixture (1/1 ratio) as yellow oil. Yield (8.0 g, 36%).

¹H NMR (400 MHz, CDCl₃): δ 4.63-4.25 (m, 1H), 2.99-2.71 (m, 1H), 2.13-1.62 (m, 4H), 1.52-1.46 (m, 9H), 1.28-1.18 (m, 1H), 0.92-0.76 (m, 1H), 0.51-0.25 (m, 1H).

Description 7: (1R,3S,6S)-tert-butyl-3-(hydroxymethyl)-2-azabicyclo[4.1.0]heptane-2-carboxylate (D7)

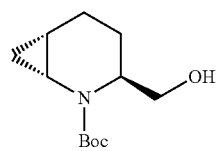 [SMILES: CC(C)(C)OC(=O)N1[C@H](CO)CC[C@H]2C[C@H]21]

To a solution of D5 (11 g, 45.6 mmol) in THF (350 mL) cooled at 0° C., BH₃ 1M in THF (90 mL, 90 mmol) was added and the mixture was stirred at room temperature for 2 hours. Methanol (50 mL) was added; this solution was concentrated and co-evaporated twice from methanol to give the title compound. Yield (11 g, 100%).

¹H NMR (400 MHz, CDCl₃): δ 0.24 (m, 1H), 0.80-0.92 (m, 1H), 1.21 (m, 4H), 1.51 (s, 9H), 1.55-1.71 (m, 4H), 1.86 (m, 1H), 2.48-2.68 (m, 1H) 3.61-4.08 (m, 3H).

ESI+ m/z 250 [M+Na]⁺

Description 8: (1R,3S,6S)-tert-butyl-3-((1,3-dioxoisoindolin-2-yl)methyl)-2-azabicyclo[4.1.0]-heptane-2-carboxylate (D8)

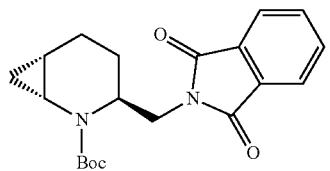 [SMILES: CC(C)(C)OC(=O)N1[C@H](CN2C(=O)c3ccccc3C2=O)CC[C@H]2C[C@H]21]

A suspension of D7 (10 g, 44 mmol), phtalimide (10.29 g, 70 mmol) and triphenylphosphine (18.34 g, 70 mmol) in THF (150 mL) was cooled at 0° C., then a 40% solution of DEAD in toluene (31.94 mL, 70 mmol) was added. The mixture was stirred at room temperature for 3 hours, then water was added and the mixture was concentrated under vacuum; the residue was dissolved in DCM, washed with water and organics were evaporated. Cyclohexane (300 mL) and DCM (10 mL) were added, the precipitate was discarded and the filtrate was concentrated. The crude mixture was purified by silica gel column chromatography (cyclohexane/ethyl acetate=95:5 to 70/30) to give the title compound as a white solid. Yield (11 g, 71%).

¹H NMR (400 MHz, CDCl₃): δ 0.18-0.28 (m, 1H), 0.76-0.96 (m, 1H), 1.11-1.18 (m, 9H), 1.30-1.40 (m, 1H), 1.48-1.57 (m, 2H), 1.69-1.83 (m, 2H), 1.95-2.09 (m, 1H), 2.73-2.83 (m, 1H), 3.49-3.54 (m, 1H), 4.01-4.09 (m, 1H), 4.23-4.03 (m, 1H), 7.68 (m, 1H), 7.74 (m, 1H) 7.83-7.89 (m, 2H).

ESI+ m/z 735 [2M+Na]⁺

Description 9: (1R,3S,6S)-tert-butyl-3-(aminomethyl)-2-azabicyclo[4.1.0]heptane-2-carboxylate (D9)

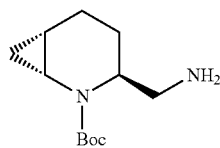 [SMILES: CC(C)(C)OC(=O)N1[C@H](CN)CC[C@H]2C[C@H]21]

To a solution of D8 (11 g, 30.9 mmol) in ethanol (200 mL) hydrazine hydrate (7.28 mL, 150 mmol) was added and the mixture was stirred at room temperature for 16 hours. The precipitate was filtered off and the filtrate was concentrated. Then i-Pr₂O was added, the precipitate was discarded and the filtrate was concentrated to give the title compound as yellow oil. Yield (6.7 g, 96%).

¹H NMR (400 MHz, CDCl₃): δ 0.20-0.27 (m, 1H), 0.77-0.89 (m, 1H), 1.16 (m, 1H), 1.50 (m, 12H), 1.62-1.68 (m, 2H), 1.82-1.91 (m, 1H), 2.65-2.75 (m, 2H), 2.81-2.86 (m, 1H), 3.72-3.90 (m, 1H). ESI+ m/z 227 [M+Na]⁺

Description 10-13: (D10-13)

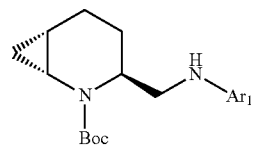

General Procedure 1

To a solution of D9 (4.5 mmol) in DMF (5 mL), K₂CO₃ (13.5 mmol) and Ar₁-X (5.4 mmol) were added. The reaction mixture was heated at 120° C. until complete conversion of the starting material. The resulting mixture was poured in water and extracted with DCM. The organic layer was concentrated to obtain a crude mixture which was purified by silica gel chromatography (cyclohexane/ethyl acetate from 10/0 to 7/3) to obtain intermediate D10-D13 as detailed in below table.

According to general procedure 1 the following intermediates were prepared:

| Intermediate | Ar1 | X | MS | Yield % |
|---|---|---|---|---|
| D10 | 5-CF₃-pyridin-2-yl | F | ESI+ m/z 372 [M + H]⁺ | 87 |
| D11 | 4-CF₃-pyridin-2-yl | F | ESI+ m/z 372 [M + H]⁺ | 84 |
| D12 | 5-Cl-pyridin-2-yl | F | ESI+ m/z: 338 [M + H]⁺ | 79 |
| D13 | 4-CF₃-pyrimidin-2-yl | Cl | ESI+ m/z 373 [M + H] | 88 |

Description 14-17 (D14-D17)

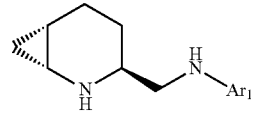

General Procedure 2

Intermediate D10-13 (1 eq.) were dissolved in dichloromethane (5 mL/mmol) and trifluoroacetic acid (2 mL/mmol) was added. After 1-16 hours at room temperature the volatiles were evaporated, the residue dissolved in dichloromethane and washed with saturated NaHCO₃ aqueous solution. The organic layers were dried over Na₂SO₄, filtered and concentrated under vacuum to obtain intermediates D14-D17 as detailed in below table.

According to general procedure 2 the following intermediates were prepared:

| Intermediate | Ar1 | MS | 1H NMR | Yield % |
|---|---|---|---|---|
| D14 | 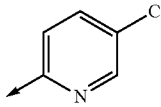 | ESI+ m/z 272 [M + H]$^+$ | $^1$HNMR (CDCl$_3$) δ ppm 8.34 (bs, 1H), 7.57 (dd, J = 2, 8 Hz, 1H), 6.45 (d, J = 8 Hz, 1H), 5.44 (m, 1H), 3.33 (m, 2H), 2.86-2.79 (m, 1H), 2.37 (m, 1H), 2.13 (m, 1H), 1.55-1.46 (m, 1H), 1.43-1.25 (m, 2H), 0.96 (m, 1H), 0.72-0.63 (m, 1H), 0.31-0.27 (m, 1H). | 89 |
| D15 | 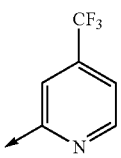 | ESI+ m/z 272 [M + H]$^+$ | $^1$HNMR (CDCl$_3$) δ ppm 8.29 (bs, 1H), 7.53 (dd, J = 2, 8 Hz, 1H), 6.47 (d, J = 8 Hz, 1H), 6.13 (m, 1H), 3.62-3.47 (m, 2H), 3.10 (m, 1H), 2.59 (m, 1H), 2.22-2.11 (m, 1H), 1.78-1.68 (m, 1H), 1.66-1.60 (m, 1H), 1.57-1.47 (m, 1H), 1.18-1.09 (m, 1H), 0.86-0.80 (m, 1H), 0.61-0.57 (m, 1H). | 100 |
| D16 | 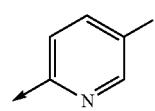 | ESI+ m/z 238 [M + H]$^+$ | $^1$HNMR (CDCl$_3$) δ ppm 10.17-9.78 (bs, 1H), 7.90 (bs, 1H), 7.58 (dd, J = 2, 8 Hz, 1H), 6.86 (d, J = 8 Hz, 1H), 3.87 (m, 1H), 3.70 (m, 1H), 3.30-3.20 (m, 1H), 2.81 (m, 1H), 2.31-2.23 (m, 1H), 1.77-1.61 (m, 3H), 1.36-1.27 (m, 1H), 1.06-0.99 (m, 1H), 0.80-0.76 (m, 1H). | 63 |
| D17 | 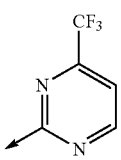 | ESI+ m/z 273 [M + H]$^+$ | $^1$HNMR (CDCl$_3$) δ ppm 10.34 (bs, 1H), 9.44 (bs, 1H), 8.47 (bs, 1H), 7.81 (bs, 1H), 6.86 (d, J = 8 Hz, 1H), 3.88-3.84 (m, 1H), 3.50 (m, 1H), 2.77 (m, 1H), 2.30 (m, 1H), 1.73-1.51 (m, 4H), 1.25 (m, 1H), 0.95 (m, 1H), 0.68 (m, 1H). | 100 |

Description 18: 2-bromo-5-cyanobenzoic acid (D18)

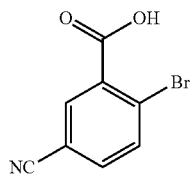

A solution of NaNO$_2$ (0.29 g, 4.2 mmol) in water (1.6 mL) was added dropwise to a solution of 5-amino-2-bromobenzoic acid (0.86 g, 4 mmol) in HCl 2N (6 mL) and water (6 mL) at 0° C. during 15 minutes. The reaction mixture was stirred for 20 minutes and then added dropwise to a solution of CuCN (0.7 g, 8 mmol) and NaCN (0.4 g, 8 mmol) in water (5 mL) at 60° C.; the mixture was heated at 60° C. for further 15 minutes. After cooling at room temperature HCl (2N) was added and the product was extracted twice with AcOEt; the combined organic layers were dried and evaporated to give the title compound as a brown solid. Yield (0.6 g, 67%).

ESI- m/z 475 [2M+Na]$^-$ $^1$H NMR (400 MHz, DMSO-d6): δ 7.89 (dd, 1H), 7.96 (d, 1H), 8.19 (d, 1H), 13.88 (br s, 1H).

Description 19-22 (D19-D22)

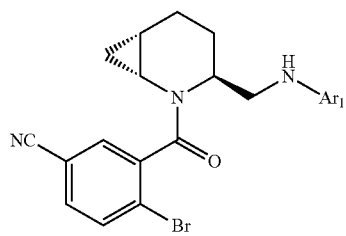

General Procedure 3

A suspension of D18 (91 mg, 0.4 mmol), N-methyl morpholine (150 μL; 1.36 mmol) and 2-chloro-4,6-dimethoxy-1,3,5-triazine (80 mg; 0.45 mmol) in dry 1,4-dioxane (1.5 mL) was stirred at 25° C. for 0.5 hours, then D14-D17 (0.4 mmol) dissolved in 1,4-dioxane (1.5 mL) were added. After 1-2 hours at 60-70° C., AcOEt and water were added; organics were dried over Na$_2$SO$_4$ and concentrated to a crude which was purified by silica gel column chromatography (DCM to DCM/MeOH 95/5) to obtain intermediate D19-D22 as detailed in below table.

According to general procedure 3 the following intermediates were prepared:

| Intermediate | Ar1 | MS | Yield % |
|---|---|---|---|
| D19 | 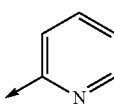 | ESI+ m/z 480 [M + H]+ | 73 |
| D20 | 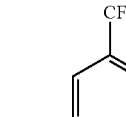 | ESI+ m/z 480 [M + H]+ | 63 |
| D21 | 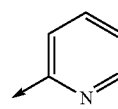 | ESI+ m/z 446 [M + H]+ | 73 |
| D22 | 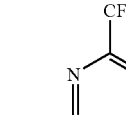 | ESI+ m/z 481 [M + H]+ | 65 |

Description 23: 5-chloro-2-iodobenzoyl chloride (D23)

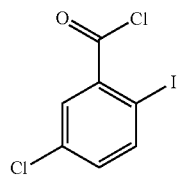 [SMILES: O=C(Cl)c1cc(Cl)ccc1I]

To a solution of 5-chloro-2-iodobenzoic acid (3.0 g, 10.6 mmol) in toluene (150 mL), SOCl$_2$ (7.75 mL, 106 mmol) was added and the mixture was heated at 100° C. for 3 hours. The solvent was concentrated in vacuum and the residue was co-evaporated from toluene twice to give the title compound as a grey solid. Yield (3.2 g, 100%)

$^1$H NMR (400 MHz, CDCl$_3$): δ 7.26 (dd, 1H), 7.98 (d, 1H), 8.03 (d, 1H).

Description 24: 5-methyl-2-iodobenzoyl chloride (D24)

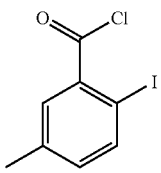

To a solution of 5-methyl-2-iodobenzoic acid (3.0 g, 11.4 mmol) in toluene (150 mL), SOCl$_2$ (8.35 mL, 114 mmol) was added and the mixture was heated at 100° C. for 3 hours. The solvent was concentrated in vacuum and the residue was co-evaporated from toluene twice to give the title compound as a grey solid. Yield (3.2 g, 100%)

$^1$H NMR (400 MHz, CDCl$_3$): δ 2.42 (s, 3H), 7.09 (dd, 1H), 7.90 (d, 1H), 7.92 (d, 1H).

Description 25-31: (D25-D31)

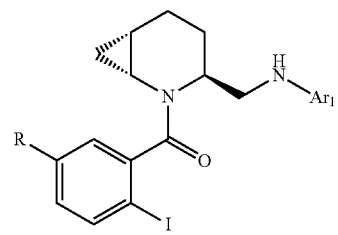

General Procedure 4

To a solution of intermediates D14-D17 (1 mmol) in DCM (2 mL) and triethylamine (2.2 mmol), a solution of D23-D24 (1 mmol) in DCM (2 mL) was added. The reaction mixture was stirred at room temperature until complete conversion of the starting material. The resulting mixture was washed with aqueous solution of NaHCO$_3$, with water, dried and evaporated.

General Procedure 5

To a solution of intermediates D14-D17 (1 mmol) in DCM (6 mL) and triethylamine (2.2 mmol), a solution of D23-D24 (1.2 mmol) in DCM (2 mL) was added. The reaction mixture was stirred at room temperature until complete conversion of the starting material. The resulting mixture was washed with aqueous solution of NaHCO$_3$, with water, dried and evaporated. Crude was purified by silica-NH chromatography (Cyclohexane/ethyl acetate from 10/0 to 5/5).

According to general procedure 4-5 the following intermediates were prepared:

| Intermediate | Ar1 | R | Procedure | MS | Yield % |
|---|---|---|---|---|---|
| D25 | 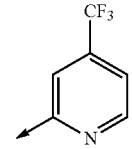 | Cl | 5 | ESI+ m/z 536 [M + H]+ | 19 |
| D26 | 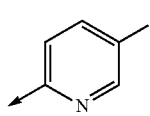 | Me | 4 | ESI+ m/z 481 [M + H]+ | 78 |
| D27 | 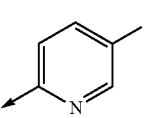 | Me | 5 | ESI+ m/z 517 [M + H]+ | 29 |
| D28 | 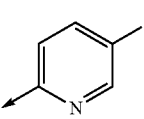 | Cl | 4 | ESI+ m/z 536 [M + H]+ | 76 |

-continued

| Intermediate | Ar1 | R | Procedure | MS | Yield % |
|---|---|---|---|---|---|
| D29 | 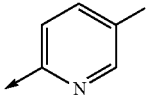 5-Cl-pyridin-2-yl | Cl | 4 | ESI+ m/z 503 [M + H]+ | 66 |
| D30 | 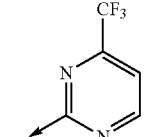 4-CF3-pyrimidin-2-yl | Cl | 4 | ESI+ m/z 537 [M + H]+ | 72 |

Description 32-34: (D32-D34)

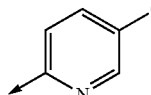

General Procedure 6

To a solution of D7 (1.32 mmol) in DMF (15 mL) cooled at 0° C., NaH 60% (1.58 mmol) was added. After stirring at room temperature for 10 minutes 2-F—Ar₁ (1.58 mmol) was added and the reaction mixture was stirred at room temperature for 2-17 hours. An aqueous solution of NaHCO₃ was added and the product was extracted with DCM, washed with brine, dried and concentrated to obtain a crude mixture which was purified by silica gel chromatography (cyclohexane/ ethyl acetate from 10/0 to 7/3).

According to general procedure 6 the following intermediates were prepared:

| Intermediate | Ar1 | MS | Yield % |
|---|---|---|---|
| D32 | 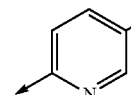 5-CF3-pyridin-2-yl | ESI+ m/z 395 [M + Na]+ | 73 |
| D33 | 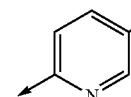 5-Cl-pyridin-2-yl | ESI+ m/z 361 [M + Na]+ | 96 |
| D34 | 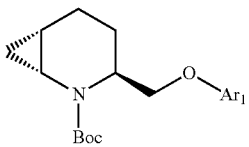 5-F-pyridin-2-yl | ESI+ m/z 345 [M + Na]+ | 47 |

Description 35-37: (D35-D37)

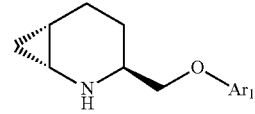

General Procedure 7

Intermediates D32-D34 (1 eq.) were dissolved in dichloromethane (10 ml/mmol) and trifluoroacetic acid (1.5 ml/mmol) was added. After 1 hour at room temperature the solution was evaporated, the residue dissolved in MeOH and loaded on a SCX cartridge, which was then washed with MeOH, followed by a solution of ammonia 2.0 M in MeOH. The basic fractions were collected and evaporated.

According to general procedure 7 the following intermediates were prepared:

| Intermediate | Ar1 | MS | 1HNMR | Yield % |
|---|---|---|---|---|
| D35 | 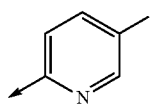 5-CF3-pyridin-2-yl | ESI+ m/z 273 [M + H]+ | ¹HNMR (CDCl₃) δ ppm 8.44 (bs, 1H), 7.78 (dd, J = 2, 8 Hz, 1H), 6.86 (d, J = 8 Hz, 1H), 4.30-4.28 (m, 2H), 3.07-3.0 (m, 1H), 2.50-2.45 (m, 1H), 2.22-2.14 (m, 1H), 1.68-1.61 (m, 2H, under water peak), 1.56-1.34 (m, 2H), 1.04-0.96 (m, 1H), 0.65-0.59 (m, 1H), 0.36-0.32 (m, 1H). | 91 |
| D36 | 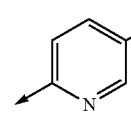 5-Cl-pyridin-2-yl | ESI+ m/z 239 [M + H]+ | ¹HNMR (CDCl₃) δ ppm 8.10 (bs, 1H), 7.53 (dd, J = 2, 8 Hz, 1H), 6.73 (d, J = 8 Hz, 1H), 4.22-4.16 (m, 2H), 3.03-2.97 (m, 1H), 2.49-2.44 (m, 1H), 2.22-2.13 (m, 1H), 1.91-1.78 (m, 1H,), 1.68-1.59 (m, 1H), 1.54-1.46(m, 1H), 1.41-1.32 (m, 1H), 1.04-0.95 (m, 1H), 0.63-0.57 (m, 1H), 0.36-0.32 (m, 1H). | 86 |
| D37 | 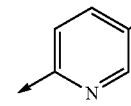 5-F-pyridin-2-yl | ESI+ m/z 223 [M + H] | ¹HNMR (CDCl₃) δ ppm 7.98 (d, J = 2 Hz, 1H), 7.37-7.32 (m, 1H), 6.74 (m, 1H), 4.21-4.15 (m, 2H), 3.04-2.98 (m, 1H), 2.49-2.45 (m, 1H), 2.21-2.13 (m, 1H), 1.84 (m, 1H,), 1.69-1.60 (m, 1H), 1.54-1.47 (m, 1H), 1.42-1.32 (m, 1H), 1.03-0.95 (m, 1H), 0.63-0.57 (m, 1H), 0.36-0.33 (m, 1H). | 79 |

Description 38-39 (D38-D39)

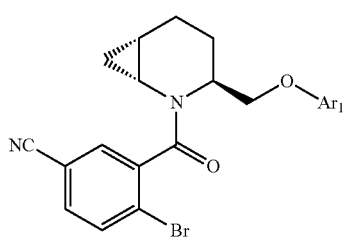

General procedure 8

A suspension of D18 (80 mg, 0.35 mmol), N-methyl morpholine (95 μl; 0.88 mmol) and 2-chloro-4,6-dimethoxy-1,3,5-triazine (56.5 mg; 0.32 mmol) in dry 1,4-dioxane (2 ml) was stirred at 25° C. for 1 hour, then (D36-D37) (0.29 mmol) dissolved in 1,4-dioxane (2 ml) were added. The reaction mixture was heated at 80° C. for 1.5 hours and concentrated in vacuum. The residue was dissolved in DCM, washed with an aqueous solution of NaHCO$_3$, with an aqueous solution of NH$_4$Cl, dried and concentrated to obtain a crude mixture which was purified by silica gel chromatography (cyclohexane/ethyl acetate 8/2).

According to general procedure 8 the following intermediates were prepared:

| Intermediate | Ar1 | Procedure | MS | Yield % |
|---|---|---|---|---|
| D38 | (5-Cl pyridin-2-yl) | 8 | ESI+ m/z 447 [M + H]$^+$ | 63 |
| D39 | (5-F pyridin-2-yl) | 8 | ESI+ m/z 431 [M + H]$^+$ | 54 |

Description 40-44: (D40-D44)

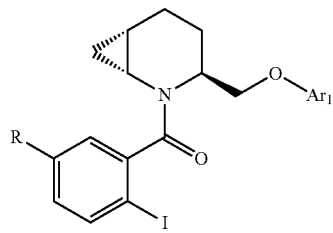

General Procedure 9

To a solution of intermediates D35-D37 (0.18 mmol) in DCM (1 mL) and thriethylamine (0.4 mmol), a solution of D23-D24 (0.18 mmol) in DCM (1 mL) was added. The reaction mixture was stirred at room temperature for 1-1.5 hours. The resulting mixture was washed with water, with aqueous solution of NaHCO$_3$, dried and evaporated.

General Procedure 10

To a solution of intermediates D35-D37 (0.18 mmol) in DCM (1 mL) and thriethylamine (0.4 mmol), a solution of D23-D24 (0.18 mmol) in DCM (1 mL) was added. The reaction mixture was stirred at room temperature for 1-1.5 hours. The resulting mixture was washed with water, with aqueous solution of NaHCO$_3$, dried and evaporated. The crude was purified by silica gel chromatography (cyclohexane/ethyl acetate 8/2).

According to general procedures 9-10 the following intermediates were prepared:

| Intermediate | Ar1 | R | Procedure | MS | Yield % |
|---|---|---|---|---|---|
| D40 | (5-F pyridin-2-yl) | Cl | 9 | ESI+ m/z 487 [M + H]$^+$ | 96 |
| D41 | (5-CF$_3$ pyridin-2-yl) | Cl | 9 | ESI+ m/z 537 [M + H]$^+$ | 95 |
| D42 | (5-Cl pyridin-2-yl) | Cl | 9 | ESI+ m/z 504 [M + H]$^+$ | 94 |
| D43 | (5-Cl pyridin-2-yl) | Me | 9 | ESI+ m/z 483 [M + H]$^+$ | 75 |
| D44 | (5-CF$_3$ pyridin-2-yl) | Me | 10 | ESI+ m/z 517 [M + H]$^+$ | 66 |

Description 45: (3S)-tert-butyl 3-(hydroxymethyl)-2-azabicyclo[4.1.0]heptane-2-carboxylate (D45)

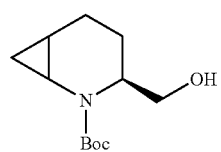 [SMILES: CC(C)(C)OC(=O)N1C2CC2CC[C@H]1CO]

To a solution of D6 (8 g, 45.6 mmol) in THF (250 mL) cooled at 0° C., BH$_3$ 1M in THF (66 mL, 66 mmol) was added and the mixture was stirred at room temperature for 2 hours. Methanol was added, the solution was concentrated in vacuum and co-evaporated twice from methanol to give the title compound as 1/1 diasteroisomeric mixture. Yield (7.6 g, 100%)

$^1$H NMR (400 MHz, CDCl$_3$): δ 3.59-4.07 (m, 3H), 2.46-2.89 (m, 1H), 1.82-2.07 (m, 1H), 1.54-1.70 (m, 4H), 1.51 (s, 9H), 0.94-1.22 (m, 1H), 0.18-0.82 (m, 1H).

ESI+ m/z 250 [M+Na]$^+$

Description 46: (3S)-tert-butyl-3-((1,3-dioxoisoindolin-2-yl)methyl)-2-azabicyclo[4.1.0]-heptane-2-carboxylate (D46)

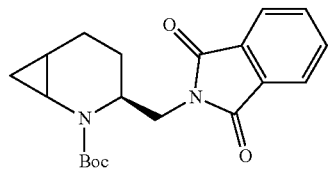 [SMILES: CC(C)(C)OC(=O)N1C2CC2CC[C@H]1CN1C(=O)c2ccccc2C1=O]

A suspension of D45 (7.6 g, 33.5 mmol), phtalimide (7.8 g, 53 mmol) and triphenylphosphine (13.9 g, 53 mmol) in THF (110 mL) was cooled at 0° C. then a 40% solution of DEAD in toluene (24 mL, 53 mmol) was added. The mixture was stirred at room temperature for 3 hours, then water was added and the mixture was concentrated under vacuum; the residue was dissolved in DCM, washed with water then organics were evaporated. Cyclohexane (237.5 mL) and DCM (12.5 mL) were added, the precipitate was discarded and the filtrate was concentrated to a crude mixture (12 g) which was used without any further purification.

ESI+ m/z 735 [2M+Na]$^+$

Description 47: (3S)-tert-butyl 3-(aminomethyl)-2-azabicyclo[4.1.0]heptane-2-carboxylate (D47)

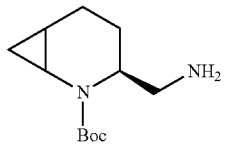 [SMILES: CC(C)(C)OC(=O)N1C2CC2CC[C@H]1CN]

To a solution of D46 (12 g, 33 mmol) in ethanol (200 mL), hydrazine hydrate (7.3 mL, 150 mmol) was added and the mixture was stirred at room temperature for 16 hours. The precipitate was filtered off and the filtrate was concentrated. Then i-Pr$_2$O was added, the precipitate was discarded and the filtrate was concentrated.

The residue was dissolved in MeOH and loaded on a SCX cartridge, which was then washed with MeOH, followed by an ammonia solution (2.0M in MeOH). The basic fractions were collected and evaporated to give a yellow oil as the title compound (disteroisomeric mixture). Yield (4.3 g, 58%)

$^1$H NMR (400 MHz, CDCl$_3$): δ 0.19-0.30 (m, 1H), 0.77-0.95 (m, 1H), 1.15-1.25 (m, 1H), 1.43-1.56 (m, 12H), 1.61-1.66 (m, 2H), 1.81-2.04 (m, 1H), 2.63-2.87 (m, 2H), 2.81-2.86 (m, 1H), 3.73-3.95 (m, 1H).

ESI+ m/z 227 [M+Na]$^+$

Description 48-51: (D48-D51)

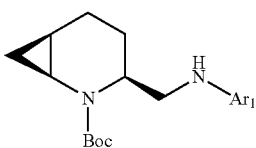

General Procedure 11

To a solution of D47 (4.86 mmol) in DMF (8 mL), K$_2$CO$_3$ (8.68 mmol) and Ar$_1$-X (where X is 2-chloro or fluoro; 5.8 mmol) were added. The reaction mixture was heated at 80-130° C. until complete conversion of the starting material. The resulting mixture was poured into aqueous solution of NH$_4$Cl and extracted with AcOEt. The organic layer was dried and concentrated to obtain a crude mixture which was purified by silica gel chromatography (cyclohexane/ethyl acetate from 10/0 to 8/2) to give the title compound as single diasteroisomer.

General Procedure 12

To a solution of D47 (6 mmol) in DMF (12 mL), K$_2$CO$_3$ (18 mmol) and Ar$_1$-X (where X is 2-chloro or fluoro; 7.2 mmol) were added. The reaction mixture was heated at 120° C. until complete conversion of the starting material. The resulting mixture was poured in water and extracted with DCM. The organic layer was concentrated to obtain a crude mixture which was purified by silica gel chromatography (cyclohexane/ethyl acetate from 10/0 to 75/25) to give the title compound as pure diasteroisomer.

According to general procedures 11-12 the following intermediates were prepared:

| Intermediate | Ar1 | X | Procedure | MS | Yield % |
|---|---|---|---|---|---|
| D48 | 5-CF$_3$-pyridin-2-yl | F | 12 | ESI+ m/z 372 [M + H]$^+$ | 38 |
| D49 | 4-CF$_3$-pyridin-2-yl | F | 11 | ESI+ m/z 372 [M + H]$^+$ | 31 |
| D50 | 5-Cl-pyridin-2-yl | F | 11 | ESI+ m/z 338 [M + H]$^+$ | 17 |
| D51 | 4-CF$_3$-pyrimidin-2-yl | Cl | 11 | ESI+ m/z 373 [M + H]$^+$ | 25 |

Description 52-55

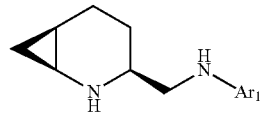

General Procedure 13

Intermediates D48-D51 (1 eq.) were dissolved in dichloromethane (3 mL/mmol) and trifluoroacetic acid (1 mL/mmol) was added. After 1.5 hours at room temperature the solution was diluted with MeOH and loaded on a SCX cartridge, which was then washed with MeOH, followed by an ammonia solution (2.0M in MeOH). The basic fractions were collected and evaporated.

General Procedure 14

Intermediates D48-D51 (1 eq.) were dissolved in dichloromethane (4 mL/mmol) and trifluoroacetic acid (2 mL/mmol) was added. After 2 hours at room temperature the solution was evaporated, the residue dissolved in dichloromethane and washed with saturated NaHCO$_3$ aqueous solution. The organic layers were dried (Na$_2$SO$_4$) and concentrated under vacuum.

According to general procedures 13-14 the following intermediates were prepared:

| Intermediate | Ar1 | Procedure | MS | ¹HNMR | Yield % |
|---|---|---|---|---|---|
| D52 | 5-CF₃-pyridin-2-yl | 14 | ESI+ m/z 273 [M + H]⁺ | ¹HNMR (CDCl₃) δ ppm 8.33 (bs, 1H), 7.56 (dd, J = 2, 8 Hz, 1H), 6.44 (d, J = 8 Hz, 1H), 5.32 (m, 1H), 3.46-3.40 (m, 1H), 3.05-2.98 (m, 1H), 2.77-2.70 (m, 1H), 2.51-2.46 (m, 1H), 2.09-1.91 (m, 2H), 1.43-1.21 (m, 1H), 1.06-0.94 (m, 2H), 0.78-0.72 (m, 1H), 0.27-0.23 (m, 1H). | 74 |
| D53 | 4-CF₃-pyridin-2-yl | 13 | ESI+ m/z 273 [M + H]⁺ | ¹HNMR (CDCl₃) δ ppm 8.21 (d, J = 2 Hz, 1H), 6.73 (d, J = 8Hz, 1H), 6.59 (s, 1H), 5.19 (m, 1H), 3.45-3.38 (m, 1H), 3.03-2.96 (m, 1H), 2.76-2.70 (m, 1H), 2.50-2.46 (m, 1H,), 2.08-1.92 (m, 2H), 1.61-1.56 (m, 1H), 1.06-0.94 (m, 2H), 0.77-0.72 (m, 1H), 0.26-0.22 (m, 1H). | 70 |
| D54 | 5-Cl-pyridin-2-yl | 13 | ESI+ m/z 238 [M + H]⁺ | ¹HNMR (CDCl₃) δ ppm 8.02 (d, J = 2 Hz, 1H), 7.34 (dd, J = 2, 8 Hz, 1H), 8.37 (d, J = 8 Hz, 1H), 4.91 (m, 1H), 3.36-3.30 (m, 1H), 2.98-2.92 (m, 1H), 2.74-2.67 (m, 1H), 2.50-2.45 (m, 1H,), 2.07-1.90 (m, 2H), 1.59-1.54 (m, 1H, under water peak), 1.04-0.93 (m, 2H), 0.76-0.70 (m, 1H), 0.25-0.21 (m, 1H). | 100 |
| D55 | 4-CF₃-pyrimidin-2-yl | 13 | ESI+ m/z 274 [M + H]⁺ | ¹HNMR (CDCl₃) δ ppm 8.48 (bs, 1H), 6.81 (d, J = 2 Hz, 1H), 5.79 (m, 1H), 3.53-3.47 (m, 1H), 3.17-3.10 (m, 1H), 2.76-2.69 (m, 1H), 2.50-2.46 (m, 1H), 2.07-1.90 (m, 2H), 1.60-1.54 (m, 1H, under water peak), 1.04-0.91 (m, 1H), 0.75-0.70 (m, 1H), 0.25-0.22 (m, 1H). | 77 |

Description 56: 4-bromo-3-((1S,3S,6R)-3-(((5-(trifluoromethyl)pyridin-2-yl)amino)methyl)-2-azabicyclo[4.1.0]heptane-2-carbonyl)benzonitrile (D56)

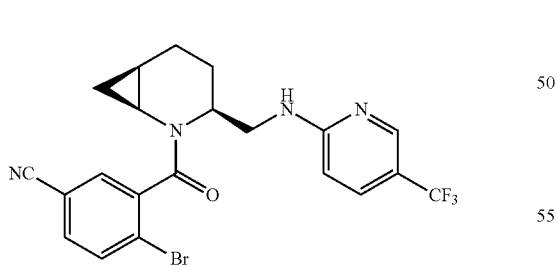

A suspension of D18 (68 mg, 0.3 mmol;), N-methyl morpholine (110 μL; 1.02 mmol) and 2-chloro-4,6-dimethoxy-1,3,5-triazine (60 mg; 0.34 mmol) in dry 1,4-dioxane (1 mL) was stirred at 25° C. for 0.5 hour, then D52 (0.3 mmol) dissolved in 1,4-dioxane (1 mL) was added. After 1 hour at 60° C., DCM and water were added. The organic layer was separated, washed with aqueous citric acid solution, washed with saturated NaHCO₃ aqueous solution and concentrated in vacuum.
ESI+ m/z 480 [M+H]⁺

Description 57-64: (D57-D64)

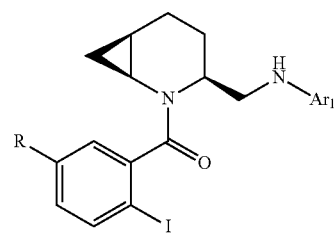

General Procedure 15
To a solution of intermediates D52-D55 (0.085 mmol) in DCM (1 mL) and triethylamine (0.17 mmol), a solution of D23-D24 (0.1 mmol) in DCM (1 mL) was added. The reaction mixture was stirred at room temperature for 2 hours then washed with water, dried and evaporated. Crude was purified by silica gel column chromatography (Cyclohexane/ethyl acetate from 10/0 to 5/5).

General Procedure 16

To a solution of intermediates D52-D55 (0.3 mmol) in DCM (5 mL) and triethylamine (0.45 mmol), a solution of D23-D24 (0.3 mmol) in DCM (2 mL) was added. The reaction mixture was stirred at room temperature for 0.5 hours then washed with water, dried and evaporated. Crude was purified by silica gel column chromatography (Cyclohexane/ethyl acetate from 10/0 to 5/5).

General Procedure 17

To a suspension of intermediates D52-D55 (0.25 mmol) and Si-diethylamine (silica supported reagent, Silicycle, loading 1.25 mmol/g, 300 mg, 0.375 mmol) in DCM (0.5 mL), a solution of D23-D24 (0.25 mmol) in DCM (0.5 mL) was added. The reaction mixture was stirred at room temperature for 2-48 hours then filtered, washed with methanol/DCM 1/1. The solution was loaded on a SCX cartridge, which was then washed with MeOH, followed by an ammonia solution (2.0M in MeOH). The ammonia eluted fractions were collected and evaporated to give the title compounds.

According to general procedure 15-17 the following intermediates were prepared:

| Intermediate | Ar1 | R | Procedure | MS | Yield % |
|---|---|---|---|---|---|
| D57 | 5-CF3-pyridin-2-yl | Me | 15 | ESI+ m/z 516 [M + H]+ | 98 |
| D58 | 5-CF3-pyridin-2-yl | Cl | 16 | ESI+ m/z 535 [M + H]+ | 87 |
| D59 | 4-CF3-pyridin-2-yl | Me | 17 | ESI+ m/z 515 [M + H]+ | 90 |
| D60 | 5-Cl-pyridin-2-yl | Cl | 17 | ESI+ m/z 502 [M + H]+ | 84 |
| D61 | 4-CF3-pyridin-2-yl | Cl | 17 | ESI+ m/z 535 [M + H]+ | 88 |
| D62 | 5-Cl-pyridin-2-yl | Me | 17 | ESI+ m/z 481 [M + H]+ | 81 |
| D63 | 4-CF3-pyrimidin-2-yl | Cl | 17 | ESI+ m/z 536 [M + H]+ | 46 |
| D64 | 4-CF3-pyrimidin-2-yl | Me | 17 | ESI+ m/z 516 [M + H]+ | 54 |

Description 65:
2-methyl-5-phenylthiazole-4-carboxylic acid (D65)

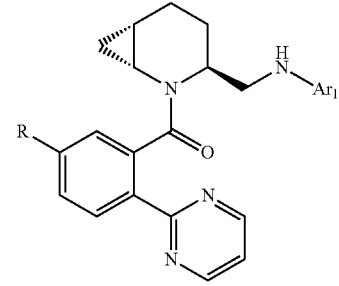

2-methyl-5-phenylthiazole-4-carboxylic acid may be prepared as in the procedure described in U.S. Pat. No. 3,282,927.

EXAMPLES

Example 1

Preparation of Compounds 1a-k

General Procedure 18

Intermediates (D19-22 and D25-31) (1 mmol) were dissolved in dry DMF (15 ml/mmol) under nitrogen atmosphere, then CsF (2 mmol), CuI (0.2 mmol), [Ph₃P]₄Pd (0.1 mmol) and pyrimidine-2-tributylstannane (1.5 mmol; prepared according to Eur. J. Org. Chem. 2003, 1711-1721) were added. The mixture was warmed at 130° C. for 10 minutes (microwave), then poured in aqueous saturated solution of NH₄Cl and extracted with AcOEt (3×50 ml). The organic layers were combined, dried (Na₂SO₄) and concentrated under vacuum; the crude mixture was purified by silica gel column chromatography (Cyclohexane 100% to Cyclohexane/Acetone 8/2 or Cyclohexane 100% to cyclohexane/AcOEt 2/8) to give the title compounds.

General Procedure 19

Intermediates (D19-22 and D25-31) (1 mmol) were dissolved in dry DMF (15 ml/mmol) under nitrogen atmosphere, General Procedure 21

Intermediates (D19-22 and D25-31) (1 mmol) were dissolved in dry DMF (15 ml/mmol) under nitrogen atmosphere, then CsF (2 mmol), CuI (0.2 mmol), [Ph$_3$P]$_4$Pd (0.1 mmol) and pyrimidine-2-tributylstannane (1.5 mmol; prepared according to *Eur. J. Org. Chem.* 2003, 1711-1721) were added. The mixture was warmed at 130° C. for 10 minutes (microwave). The reaction mixture was poured in water and extracted with DCM. The organic layers were combined, dried (Na$_2$SO$_4$) and concentrated under vacuum then purified by silica-NH column chromatography (Cyclohexane 100% to cyclohexane/AcOEt 2/8) to give a residue that was dissolved in MeOH then loaded on a SCX cartridge, which was then washed with MeOH, followed by a solution of ammonia 2.0 M in MeOH. The basic fractions were collected and evaporated to give the title compounds.

General Procedure 20

Intermediates (D19-22 and D25-31) (1 mmol) were dissolved in dry DMF (15 ml/mmol) under nitrogen atmosphere, then CsF (2 mmol), CuI (0.2 mmol), [Ph$_3$P]$_4$Pd (0.1 mmol) and pyrimidine-2-tributylstannane (1.5 mmol; prepared according to *Eur. J. Org. Chem.* 2003, 1711-1721) were added. The mixture was warmed at 100° C. for 20 minutes (microwave), then poured in aqueous saturated solution of NH$_4$Cl and extracted with DCM. The organic layers were combined, dried (Na$_2$SO$_4$) and concentrated under vacuum; the residue was dissolved in MeOH then loaded on a SCX cartridge, which was then washed with MeOH, followed by a solution of ammonia 2.0 M in MeOH. The basic fractions were collected and evaporated. The residue was purified by silica gel column chromatography (Cyclohexane 100% to Cyclohexane/Acetone 7/3) to give the title compounds.

General Procedure 21

Intermediates (D19-22 and D25-31) (1 mmol) were dissolved in dry DMF (15 ml/mmol) under nitrogen atmosphere, then CsF (2 mmol), CuI (0.2 mmol), [Ph$_3$P]$_4$Pd (0.1 mmol) and pyrimidine-2-tributylstannane (1.5 mmol; prepared according to *Eur. J. Org. Chem.* 2003, 1711-1721) were added. The mixture was warmed at 130° C. for 10 minutes (microwave). The reaction mixture was poured in water and extracted with DCM. The organic layers were combined, dried (Na$_2$SO$_4$) and concentrated under vacuum then purified by silica-NH column chromatography (Cyclohexane 100% to cyclohexane/AcOEt 2/8) to give a residue that was dissolved in MeOH then loaded on a SCX cartridge, which was then washed with MeOH, followed by a solution of ammonia 2.0 M in MeOH. The basic fractions were collected and evaporated to give the title compounds.

General Procedure 22

Intermediates (D19-22 and D25-31) (1 mmol) were dissolved in dry DMF (15 ml/mmol) under nitrogen atmosphere, then CsF (2 mmol), CuI (0.2 mmol), [Ph$_3$P]$_4$Pd (0.1 mmol) and pyrimidine-2-tributylstannane (1.5 mmol; prepared according to *Eur. J. Org. Chem.* 2003, 1711-1721) were added. The mixture was warmed at 130° C. for 10 minutes (microwave), then poured in water and extracted with DCM. The organic layers were combined, dried (Na$_2$SO$_4$) and concentrated under vacuum; the crude mixture was purified by silica gel column chromatography (Cyclohexane 100% to cyclohexane/Acetone 7/3) to give a residue that was dissolved in MeOH then loaded on a SCX cartridge, which was then washed with MeOH, followed by an ammonia solution (2.0M in MeOH). The basic fractions were collected and evaporated to give the title compounds.

Compounds 1a-k were prepared according to general procedure 18-22:

| Comp. | Intermediate | Procedure | Yield % |
| --- | --- | --- | --- |
| 1a | (D25) | 18 | 39 |

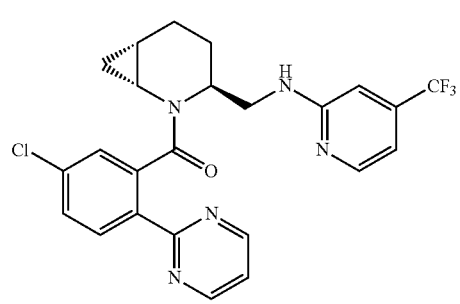 [SMILES: O=C(c1cc(Cl)ccc1-c1ncccn1)N1[C@H](CNc2cc(C(F)(F)F)ccn2)CC[C@H]2C[C@H]21]

$^1$H NMR (Acetone-d6) δ ppm = 8.89-8.80 (m, 2 H), 8.36-8.01 (m, 2 H), 7.57-7.35 (m, 3 H), 6.80-6.77 (m, 2 H), 4.62 (m, 1 H), 3.82-3.72 (m, 2 H), 2.96-2.62 (m, 1 H), 2.22-2.10 (m, 1 H), 1.91-1.82 (m, 1 H), 1.77-1.64 (m, 1H), 1.44-1.25 (m, 2H), 0.61-0.38 (m, 2H).
ESI+ m/z 488 [M + H]$^+$ (5-chloro-2-(pyrimidin-2-yl)phenyl)((1R,3S,6S)-3-(((4-(trifluoromethyl)pyridin-2-yl)amino)methyl)-2-azabicyclo[4.1.0]heptan-2-yl)methanone

| 1b | (D19) | 22 | 5 |
| --- | --- | --- | --- |

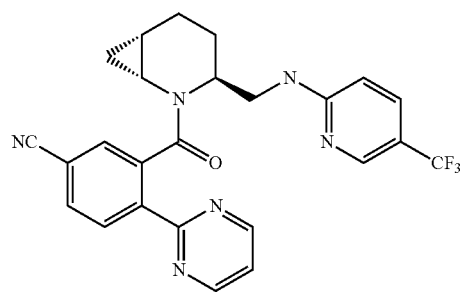 [SMILES: N#Cc1ccc(-c2ncccn2)c(C(=O)N2[C@H](CNc3ccc(C(F)(F)F)cn3)CC[C@H]3C[C@H]32)c1]

$^1$H NMR (CDCl$_3$) δ ppm 8.66-8.62 (m, 2H), 8.54-8.52 (m, 1H), 8.40 (m, 1H), 7.88-7.81 (m, 2H), 7.59-7.56 (m, 1H), 7.51-7.46 (m, 1H), 7.17-7.12 (m, 1H), 4.77-4.70 (m, 1H), 3.87-3.78 (m, 1H), 3.76-3.57 (m, 2H), 2.61-2.53 (m, 1H), 2.16-2.01 (m, 1H), 1.95-1.78 (m, 2H), 1.75-1.62 (m, 1H), 1.36-1.28 (m, 1H), 0.63-0.17 (m, 2H).
ESI+ m/z 479 [M + H]$^+$ 4-(pyrimidin-2-yl)-3-((1R,3S,6S)-3-(((5-(trifluoromethyl)pyridin-2-yl)amino)methyl)-2-azabicyclo[4.1.0]heptane-2-carbonyl)benzonitrile -continued

| Comp. | Intermediate | Procedure | Yield % |
|---|---|---|---|
| 1c | (D26) | 18 | 11 |

¹HNMR (CDCl₃) δ ppm 8.86-8.62 (m, 2H), 8.29-8.27 (m, 1H), 8.07 (m, 1H), 7.33-7.31 (m, 2H), 7.07 (m, 2H), 6.46-6.34 (m, 1H), 5.93-5.75 (m, 1H), 4.76-4.74 (m, 1H), 3.76 (m, 1H), 3.61-3.42 (m, 1H), 2.49-2.35 (m, 5H), 2.07-1.99 (m, 1H), 1.74-1.22 (m, 2H), 1.33-1.09 (m, 1H), 0.58-0.05 (m, 2H)
ESI+ m/z 434 [M + H]⁺

((1R,3S,6S-3-(((5-chloropyridin-2-yl)amino)methyl)-2-azabicyclo[4.1.0]heptan-2-yl)(5-methyl-2-(pyrimidin-2-yl)phenyl)methanone

| 1d | (D27) | 21 | 18 |
|---|---|---|---|

¹H NMR (Acetone-d6) δ ppm = 8.85-8.77 (m, 2 H), 8.36-8.09 (m, 2 H), 7.67-7.54 (m, 1 H), 7.28-7.25 (m, 2 H), 6.67-6.47 (m, 2 H), 4.64 (m, 1 H), 3.82-3.63 (m, 2 H), 2.96-2.61 (m, 1 H), 3.43-2.31 (m, 3 H), 2.18-2.10 (m, 1H), 1.91-1.82 (m, 1H), 1.73-1.61 (m, 2 H), 1.42-1.29 (m, 2 H), 0.57-0.27 (m, 2H).
ESI+ m/z 468 [M + H]⁺

(5-methyl-2-(pyrimidin-2-yl)phenyl)((1R,3S,6S)-3-(((5-(trifluoromethyl)pyridin-2-yl)amino)methyl)-2-azabicyclo[4.1.0]heptan-2-yl)methanone

| 1e | (D28) | 21 | 11 |
|---|---|---|---|

¹H NMR (Acetone-d6) δ ppm = 8.89-8.82 (m, 2 H), 8.37-8.17 (m, 2 H), 7.67-7.57 (m, 2 H), 7.46-7.37 (m, 2 H), 6.68-6.54 (m, 1 H), 4.62 (m, 1 H), 3.80-3.68 (m, 2H), 2.95-2.82 (m, 1H), 2.22-2.10 (m, 1H), 1.91-1.82 (m, 1H), 1.75-1.68 (m, 2H), 1.48-1.34 (m, 2H), 0.80-0.31 (m, 2H).
ESI+ m/z 488 [M + H]⁺

(5-chloro-2-(pyrimidin-2-yl)phenyl)((1R,3S,6S)-3-(((5-(trifluoromethyl)pyridin-2-yl)amino)methyl)-2-azabicyclo[4.1.0]heptan-2-yl)methanone

| 1f | (D29) | 21 | 29 |
|---|---|---|---|

¹H NMR (Acetone-d6) δ ppm = 8.89-8.82 (m, 2 H), 8.36-8.19 (m, 1 H), 8.02-7.74 (m, 1 H), 7.59-7.31 (m, 3 H), 6.58-6.43 (m, 1 H), 6.24-6.14 (m, 1 H), 4.60 (m, 1H), 3.72-3.60 (m, 2H), 2.95-2.60 (m, 1H), 2.18-2.09 (m, 1H), 1.88-1.84 (m, 1H), 1.73-1.63 (m, 2H), 1.40-1.32 (m, 1H), 1.22-0.9 (m, 1H), 0.63-0.33 (m, 2H).
ESI+ m/z 455 [M + H]⁺

(5-chloro-2-(pyrimidin-2-yl)phenyl)((1R,3S,6S)-3-(((5-chloropyridin-2-yl)amino)methyl)-2-azabicyclo[4.1.0]heptan-2-yl)methanone -continued

| Comp. | Intermediate | Procedure | Yield % |
|---|---|---|---|
| 1g | (D30) | 21 | 14 |

¹H NMR (Acetone-d6) δ ppm = 8.90-8.83 (m, 2 H), 8.69-8.58 (m, 1 H), 8.38-8.35 (m, 1 H), 7.59-7.37 (m, 2 H), 7.13-6.90 (m, 2 H), 4.70 (m, 1H), 3.84-3.71 (m, 2H), 2.98-2.65 (m, 1H), 2.20-2.10 (m, 1H), 1.91-1.84 (m, 1H), 1.78-1.70 (m, 2H), 1.40-1.29 (m, 2H), 0.60-0.36 (m, 2H).
ESI+ m/z 489 [M + H]+

(5-chloro-2-(pyrimidin-2-yl)phenyl)((1R,3S,6S)-3-(((4-(trifluoromethyl)pyrimidin-2-yl)amino)methyl)-2-azabicyclo[4.1.0]heptan-2-yl)methanone

| 1h | (D20) | 21 | 6 |
|---|---|---|---|

¹H NMR (Acetone-d6) δ ppm = 8.95-8.87 (m, 2 H), 8.51-8.35 (m, 1 H), 8.29-8.27 (m, 1 H), 7.97-7.84 (m, 2 H), 7.52-7.43 (m, 1 H), 6.80-6.77 (m, 1 H), 6.71-6.45 (m, 1H), 4.64 (m, 1H), 3.86-3.68 (m, 2H), 2.96-2.65 (m, 1H), 2.22-2.09 (m, 1H), 1.91-1.86 (m, 1H), 1.77-1.67 (m, 2H), 1.44-1.31 (m, 2H), 0.63-0.41 (m, 2H).
ESI+ m/z 479 [M + H]+

4-(pyrimidin-2-yl)-3-((1R,3S,6S)-3-(((4-(trifluoromethyl)pyridin-2-yl)amino)methyl)-2-azabicyclo[4.1.0]heptane-2-carbonyl)benzonitrile

| 1i | (D21) | 19 | 7 |
|---|---|---|---|

¹HNMR (CDCl₃) δ ppm 8.83-8.82 (m, 2H), 8.58-8.56 (m, 1H), 7.87-7.72 (m, 4H), 7.52-7.49 (m, 1H), 7.33-7.30 (m, 1H), 4.48-4.38 (m, 1H), 3.83-3.80 (m, 1H), 3.60-3.54 (m, 1H), 2.49-2.45 (m, 1H), 2.19-2.13 (m, 1H), 1.93-1.88 (m, 1H), 1.75-1.64 (m, 2H), 1.33-1.26 (m, 1H), 0.59-0.15 (m, 2H).
ESI+ m/z 445 [M + H]+

3-((1R,3S,6S)-3-(((5-chloropyridin-2-yl)amino)methyl)-2-azabicyclo[4.1.0]heptane-2-carbonyl)-4-(pyrimidin-2-yl)benzonitrile

| 1j | (D22) | 19 | 10 |
|---|---|---|---|

1HNMR (CDCl₃) δ ppm 8.85-8.84 (m, 2H), 8.56-8.34 (m, 2H), 7.82-7.73 (m, 1H), 7.54-7.71 (m, 1H), 6.89-6.83 (m, 1H), 6.22-6.12 (m, 1H), 4.77 (m, 1H), 3.72-3.89 (m, 2H), 2.57-2.47 (m, 1H), 2.18-2.06 (m, 1H), 1.91-1.77 (m, 2H), 1.69-1.60 (m, 1H), 1.48-1.28 (m, 2H), 0.64-0.21 (m, 2H).
ESI+ m/z 480 [M + H]+

4-(pyrimidin-2-yl)-3-((1R,3S,6S)-3-(((4-(trifluoromethyl)pyrimidin-2-yl)amino)methyl)-2-azabicyclo[4.1.0]heptane-2-carbonyl)benzonitrile

| Comp. | Intermediate | Procedure | Yield % |
|---|---|---|---|
| 1k | (D31) | 20 | 18 |

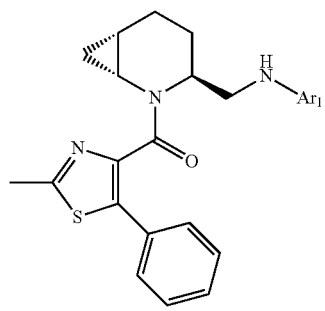

$^1$H NMR (Acetone-d6) δ ppm = 8.85-8.78 (m, 2 H), 8.69-8.57 (m, 1 H), 8.27-8.10 (m, 1 H), 7.39-7.34 (m, 1 H), 7.31-7.27 (m, 1 H), 7.13-7.01 (m, 1 H), 6.99-6.89 (m, 1H), 4.72 (m, 1H), 3.82-3.74 (m, 2H), 2.64-2.57 (m, 1H), 2.38-2.43 (m, 3H), 2.16-2.09 (m, 1H), 1.91-1.86 (m, 1H), 1.76-1.65 (m, 2H), 1.42-1.31 (m, 2H), 0.59-0.33 (m, 2H).
ESI+ m/z 469 [M + H]$^+$ (5-methyl-2-(pyrimidin-2-yl)phenyl)((1R,3S,6S)-3-(((4-(trifluoromethyl)pyrimidin-2-yl)amino)methyl)-2-azabicyclo[4.1.0]heptan-2-yl)methanone

Example 2

Preparation of Compounds 2a-c

General Procedure 23

D65 (0.06 mmol), N-methyl morpholine (0.20 mmol) and 2-chloro-4,6-dimethoxy-1,3,5-triazine (0.06 mmol) dissolved in dry 1,4-dioxane (0.5 mL) were stirred at 25° C. for 0.5 hours, then (D14-D17) (0.06 mmol) dissolved in 1,4-dioxane (0.5 mL) were added. After 2-16 hours at 60° C. the crude reaction mixture was purified by silica gel column chromatography (Cyclohexane to DCM/MeOH=9/1).

General Procedure 24

D65 (0.1 mmol), N-methyl-morpholine (0.30 mmol) and 2-chloro-4,6-dimethoxy-1,3,5-triazine (0.1 mmol) dissolved in dry 1,4-dioxane (0.5 mL) were stirred at 25° C. for 0.5 hours, then (D14-D17) (0.06 mmol) dissolved in 1,4-dioxane (0.5 mL) were added. After 2 hours at 60° C. the reaction mixture was diluted with DCM, washed with water and concentrated. The crude was purified by silica gel column chromatography (Cyclohexane to AcOEt or DCM to DCM/MeOH 95/5).

Compounds 2a-c were prepared according to general procedures 23-24:

| Comp. | Intermediate | Procedure | Yield % |
|---|---|---|---|
| 2a | (D14) | 23 | 78 |

$^1$H NMR (CDCl$_3$) δ ppm 8.25-8.36 (m, 1H), 7.22-7.58 (m, 6H), 6.42-6.54 (m, 1H), 5.85-5.96 (m, 1H), 4.73-4.78 (m, 1H), 3.64-3.74 (m, 1H), 3.42-3.54 (m, 1H), 3.07-3.31 (m, 1H), 2.59-2.74 (m, 3H), 1.64-2.38 (m, 2H), 1.49-1.57 (m, 1H), 1.30-1.40 (m, 1H), 1.06-1.15 (m, 1H), 0.39-0.69 (m, 1H), −0.04-0.24 (m, 1H).
ESI+ m/z 473 [M + H]$^+$ (2-methyl-5-phenylthiazol-4-yl)((1R,3S,6S)-3-(((5-(trifluoromethyl)pyridin-2-yl)amino)methyl)-2-azabicyclo[4.1.0]heptan-2-yl)methanone

| Comp. | Intermediate | Procedure | Yield % |
|---|---|---|---|
| 2b | (D16) | 24 | 36 |

¹H NMR (CDCl₃) δ ppm 7.91 -8.02 (m, 1H), 7.48 (m, 1H), 7.36-7.45 (m, 3H), 7.24-7.33 (m, 2H), 6.30-6.58 (m, 1H), 5.58-5.80 (m, 1H), 4.03-4.70 (m, 1H), 3.55-3.70 (m, 1H), 3.30-3.42 (m, 1H), 3.07-3.22 (m, 1H), 2.61-2.74 (m, 3H), 1.80-2.33 (m, 1H), 1.59-1.69 (m, 1H), 1.40-1.55 (m, 1H), 1.32-1.36 (m, 1H), 1.04-1.15 (m, 1H), 0.36-0.59 (m, 1H), −0.07-0.22 (m, 1H).
ESI+ m/z 439 [M + H]⁺

((1R,3S,6S)-3-(((5-chloropyridin-2-yl)amino)methyl)-2-azabicyclo[4.1.0]heptan-2-yl)(2-methyl-5-phenylthiazol-4-yl)methanone

| 2c | (D17) | 24 | 53 |
|---|---|---|---|

¹H NMR (CDCl₃) δ ppm 8.44-8.50 (m, 1H), 7.28-7.52 (m, 5H), 6.80-6.84 (m, 1H), 4.77-6.12 (m, 1H), 3.47-3.74 (m, 2H), 3.10-3.31 (m, 1H), 2.63-2.74 (m, 3H), 1.88-2.33 (m, 2H), 1.25-1.67 (m, 3H), 1.08 (m, 1H), 0.39-0.89 (m, 1H), −0.02-0.24 (m, 1H).
ESI+ m/z 474 [M + H]⁺

(2-methyl-5-phenylthiazol-4-yl)((1R,3S,6S)-3-(((4-(trifluoromethyl)pyrimidin-2-yl)amino)methyl)-2-azabicyclo[4.1.0]heptan-2-yl)methanone

Example 3

Preparation of Compounds 3a-q

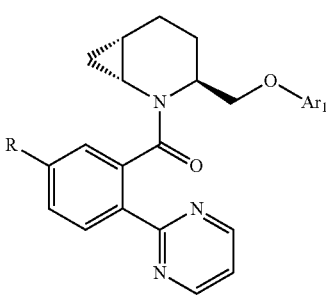

General Procedure 25

Intermediates (D38-D44) (1 mmol) were dissolved in dry DMF (15 ml/mmol) under nitrogen atmosphere, then CsF (2 mmol), CuI (0.2 mmol), [Ph₃P]₄Pd (0.1 mmol) and pyrimidine-2-tributylstannane (1.5 mmol; prepared according to Eur. J. Org. Chem. 2003, 1711-1721) were added. The mixture was heated at 100° C. for 10-20 minutes (microwave), then poured in water and extracted with DCM; the organic layers were combined, dried (Na₂SO₄) and concentrated under vacuum. The crude mixture was purified by silica gel column chromatography (Cyclohexane 100% to cyclohexane/AcOEt=1/1 or cyclohexane 100% to cyclohexane/Acetone=8/2) to give a residue that was dissolved in MeOH then loaded on a SCX cartridge, which was then washed with MeOH, followed by a solution of ammonia 2.0 M in MeOH. The ammonia eluted fractions were collected and evaporated to give the title compounds.

General Procedure 26

Intermediates (D38-D44) (1 mmol) were dissolved in dry DMF (15 ml/mmol) under nitrogen atmosphere, then CsF (2 mmol), CuI (0.2 mmol), [Ph₃P]₄Pd (0.1 mmol) and pyrimidine-2-tributylstannane (1.5 mmol; prepared according to Eur. J. Org. Chem. 2003, 1711-1721) were added. The mixture was heated at 100° C. for 30 minutes (microwave), then at 120° C. for 18 hours. The reaction mixture was poured in water and extracted with DCM; the organic layers were combined, dried (Na₂SO₄) and concentrated under vacuum. The residue was purified by silica gel column chromatography (Cyclohexane 100% to Cyclohexane/AcOEt=1/1) to give the title compounds.

Compounds 3a-g were prepared according to general procedure 25-26:

| Comp. | Intermediate | Procedure | Yield % |
|---|---|---|---|
| 3a | (D38) | 25 | 21 |

$^1$H NMR (Acetone-d6) δ ppm = 9.02-8.96 (m, 2 H), 8.52-8.41 (m, 1 H), 8.28-8.26 (m, 1 H), 8.0-7.90 (m, 2 H), 7.78-7.75 (m, 1 H), 7.56-7.53 (m, 1 H), 6.92-6.88 (m, 1 H), 4.74-4.72 (m, 1 H), 4.65-4.61 (m, 1 H), 4.52-4.47 (m, 1H), 2.70-2.61 (m, 1H), 2.03-1.95 (m, 1H), 1.86-1.69 (m, 2H), 1.45-1.31 (m, 2H), 0.68-0.43 (m, 2H).
ESI+ m/z 446 [M + H]$^+$ 3-((1R,3S,6S)-3-(((5-chloropyridin-2-yl)oxy)methyl)-2-azabicyclo[4.1.0]heptane-2-carbonyl)-4-(pyrimidin-2-yl)benzonitrile

| | | | |
|---|---|---|---|
| 3b | (D39) | 26 | 16 |

$^1$H NMR (Acetone-d6) δ ppm = 9.02-8.96 (m, 2 H), 8.52-8.41 (m, 1 H), 8.18-8.16 (m, 1 H), 7.98-7.90 (m, 2 H), 7.63-7.58 (m, 1 H), 7.55-7.52 (m, 1 H), 6.90-6.87(m, 1 H), 4.77-4.70 (m, 1 H), 4.63-4.59 (m, 1 H), 4.50-4.45 (m, 1H), 2.67-2.60 (m, 1H), 2.03-1.95 (m, 1H), 1.80-1.66 (m, 2H), 1.41-1.31 (m, 2H), 0.67-0.44 (m, 2H).
ESI+ m/z 430 [M + H]$^+$ 3-((1R,3S,6S)-3-(((5-fluoropyridin-2-yl)oxy)methyl)-2-azabicyclo[4.1.0]heptane-2-carbonyl)-4-(pyrimidin-2-yl)benzonitrile

| | | | |
|---|---|---|---|
| 3c | (D40) | 25 | 25 |

$^1$HNMR (Acetone-d6) δ ppm 8.96-8.90 (m, 2H), 8.37-8.26 (m, 1H), 8.17-7.91 (m, 1H), 7.63-7.56 (m, 1H), 7.47-7.45 (dd, 2H), 6.90-6.87 (m, 1H), 4.74-4.70 (m, 1H), 4.65-4.60 (m, 1H), 4.48-4.25 (m, 1H), 2.95-2.58 (m, 1H), 2.04-1.97 (m, 1H), 1.81-1.67 (m, 2H), 0.61-0.42 (m, 4H).
ESI+ m/z 439 [M + H]$^+$ (5-chloro-2-(pyrimidin-2-yl)phenyl)((1R,3S,6S)-3-(((5-fluoropyridin-2-yl)oxy)methyl)-2-azabicyclo-[4.1.0]heptan-2-yl)methanone

| | | | |
|---|---|---|---|
| 3d | (D41) | 25 | 20 |

$^1$H NMR (CDCl$_3$) δ ppm = 8.87-8.80 (m, 2 H), 8.52-8.34 (m, 1 H), 8.39-8.28 (m, 1 H), 7.83-7.80 (m, 1 H), 7.55-7.38 (m, 2 H), 7.24-7.22 (m, 1 H), 6.90-6.87 (m, 1 H), 4.93-4.87 (m, 1 H), 4.71-4.67 (m, 1 H), 4.57-4.25 (m, 1H), 2.54-2.49 (m, 1H), 2.06-1.99 (m, 2 H), 1.78-1.70 (m, 1H), 1.31-1.12 (m, 2H), 0.62-0.27 (m, 2H).
ESI+ m/z 489 [M + H]$^+$ (5-chloro-2-(pyrimidin-2-yl)phenyl)((1R,3S,6S)-3-(((5-(trifluoromethyl)pyridin-2-yl)oxy)methyl)-2-azabicyclo[4.1.0]heptan-2-yl)methanone -continued

| Comp. | Intermediate | Procedure | Yield % |
|---|---|---|---|
| 3e | (D42) | 25 | 60 |

¹H NMR (CDCl₃) δ ppm = 8.86-8.79 (m, 2 H), 8.38-8.28 (m, 1 H), 8.18-7.99 (m, 1 H), 7.58-7.55 (m, 1 H), 7.50-7.47 (m, 1 H), 7.37 (m, 1 H), 7.23-7.21 (m, 1H), 6.80-6.75 (m, 1H), 4.91-4.84 (m, 1H), 4.62-4.54 (m, 1H), 4.48-4.43 (m, 1H), 2.52-2.48 (m, 1H), 2.07-1.97 (m, 2H), 1.78-1.69 (m, 1H), 1.44-1.20 (m, 2H), 0.62-0.24 (m, 2H).
ESI+ m/z 456 [M + H]⁺

(5-chloro-2-(pyrimidin-2-yl)phenyl)((1R,3S,6S)-3-(((5-chloropyridin-2-yl)oxy)methyl)-2-azabicyclo[4.1.0]heptan-2-yl)methanone

| 3f | (D43) | 25 | 37 |
|---|---|---|---|

¹H NMR (CDCl₃) δ ppm = 8.84-8.78 (m, 2 H), 8.30-8.21 (m, 1 H), 8.17-7.94 (m, 1 H), 7.58-7.51(m, 1 H), 7.35-7.31 (m, 1 H), 7.18-7.15 (m, 2 H), 6.78-6.63 (m, 1H), 4.92 (m, 1H), 4.63-4.59 (m, 1H), 4.46-4.41 (m, 1H), 2.50-2.40 (m, 4H), 2.04-1.98 (m, 2H), 1.81-1.65 (m, 1H), 1.43-1.17 (m, 2H), 0.62-0.11 (m, 2H).
ESI+ m/z 435 [M + H]⁺

((1R,3S,6S)-3-(((5-chloropyridin-2-yl)oxy)methyl)-2-azabicyclo[4.1.0]heptan-2-yl)(5-methyl-2-(pyrimidin-2-yl)phenyl)methanone

| 3g | (D44) | 25 | 46 |
|---|---|---|---|

¹H NMR (CDCl₃) δ ppm = 8.85-8.78 (m, 2 H), 8.52 (m, 1 H), 8.31-8.21 (m, 1 H), 7.83-7.76 (m, 1 H), 7.34-7.30 (m, 1 H), 7.20-7.17 (m, 2 H), 6.90-6.75 (m, 1H), 4.98-4.90 (m, 1H), 4.72-4.69 (m, 1H), 4.56-4.51 (m, 1H), 2.51-2.39 (m, 4H), 2.06-1.96 (m, 2H), 1.82-1.67 (m, 1H), 1.43-1.18 (m, 2H), 0.63-0.10 (m, 2H).
ESI+ m/z 435 [M + H]⁺

(5-methyl-2-(pyrimidin-2-yl)phenyl)((1R,3S,6S)-3-(((5-(trifluoromethyl)pyridin-2-yl)oxy)methyl)-2-azabicyclo[4.1.0]heptan-2-yl)methanone

Example 4

Preparation of Compounds 4a-i

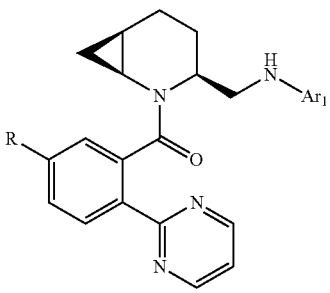

General Procedure 27

Intermediates (056-064) (1 mmol) were dissolved in dry DMF (15 ml/mmol) under nitrogen atmosphere, then CsF (2 mmol), CuI (0.2 mmol), [Ph$_3$P]$_4$Pd (0.1 mmol) and pyrimidine-2-tributylstannane (1.5 mmol; prepared according to Eur. J. Org. Chem. 2003, 1711-1721) were added. The mixture was heated at 130° C. for 10 minutes (microwave), then poured in water and extracted with DCM; the organic layers were combined, dried (Na$_2$SO$_4$) and concentrated under vacuum. The crude mixture was purified by silica gel column chromatography (Cyclohexane 100% to Cyclohexane/Acetone 7/3) to give a residue that was dissolved in MeOH then loaded on a SCX cartridge, which was then washed with MeOH, followed by an ammonia solution (2.0M in MeOH). The ammonia eluted fractions were collected and evaporated to give the title compounds.

General Procedure 28

Intermediates (056-064) (1 mmol) were dissolved in dry DMF (15 ml/mmol) under nitrogen atmosphere, then CsF (2 mmol), CuI (0.2 mmol), [Ph$_3$P]$_4$Pd (0.1 mmol) and pyrimidine-2-tributylstannane (1.5 mmol; prepared according to Eur. J. Org. Chem. 2003, 1711-1721) were added. The mixture was heated at 130° C. for 10 minutes (microwave), then poured in water and extracted with DCM; the organic layers were combined, dried (Na$_2$SO$_4$) and concentrated under vacuum. The crude mixture was dissolved in MeOH then loaded on a SCX cartridge, which was then washed with MeOH, followed by an ammonia solution (2.0M in MeOH). The basic fractions were collected and evaporated; the residue was purified by silica gel column chromatography (Cyclohexane 100% to cyclohexane/AcOEt=1/1) to give the title compounds.

General Procedure 29

Intermediates (056-064) (1 mmol) were dissolved in dry DMF (15 ml/mmol) under nitrogen atmosphere, then CsF (2 mmol), CuI (0.2 mmol), [Ph$_3$P]$_4$Pd (0.1 mmol) and pyrimidine-2-tributylstannane (1.2 mmol; prepared according to Eur. J. Org. Chem. 2003, 1711-1721) were added. The mixture was heated at 120° C. for 18 hours, then poured in aqueous saturated solution of NaHCO$_3$ and extracted with DCM. The organic layers were filtered over a celite pad, dried (Na$_2$SO$_4$) and concentrated under vacuum; the crude mixture was dissolved in MeOH then loaded on a SCX cartridge, which was then washed with MeOH, followed by an ammonia solution (2.0M in MeOH). The basic fractions were collected and evaporated; the residue was purified by silica-NH column chromatography (Cyclohexane 100% to Cyclohexane/AcOEt=1/1) to give the title compounds.

Compounds 4a-i were prepared according to general procedure 27-29:

| Comp. | Intermediate | Procedure | Yield % |
|---|---|---|---|
| 4a | (D57) | 28 | 32 |

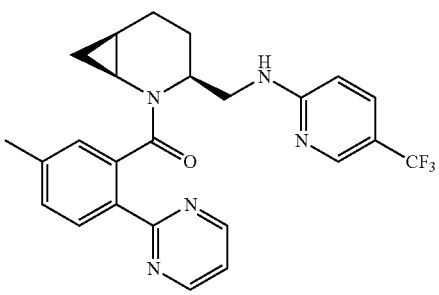 [SMILES: Cc1ccc(-c2ncccn2)c(C(=O)N2[C@H](CNc3ccc(C(F)(F)F)cn3)CC[C@@H]3C[C@@H]32)c1]

$^1$H NMR (CDCl$_3$) δ ppm = 8.64 (br. s., 2 H), 8.35-8.26 (m, 2 H), 7.56-7.54 (m, 1 H), 7.35-7.31 (m, 1H), 7.30-7.13 (m, 2 H, under the solvent peak), 6.70 (br.s., 1 H), 4.71 (br.s., 1 H), 3.78-3.43 (m, 2 H), 2.58-2.39 (m, 4 H), 2.10-2.04 (m, 1 H), 1.84-1.79 (m, 1H), 1.76-1.62 (m, 2H), 1.54-1.40 (m, 1H), 1.14-0.99 (m, 1H), 0.56-0.02 (m, 1H), −.027--0.83 (m, 1H).
ESI+ m/z 468 [M + H]$^+$ (5-methyl-2-(pyrimidin-2-yl)phenyl)((1S,3S,6R)-3-(((5-(trifluoromethyl)pyridin-2-yl)amino)methyl)-2-azabicyclo[4.1.0]heptan-2-yl)methanone

| | | | |
|---|---|---|---|
| 4b | (D58) | 27 | 15 |

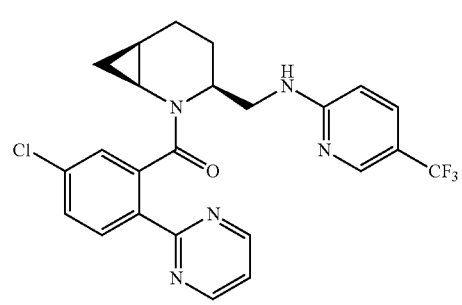 [SMILES: O=C(c1cc(Cl)ccc1-c1ncccn1)N1[C@H](CNc2ccc(C(F)(F)F)cn2)CC[C@@H]2C[C@@H]21]

$^1$H NMR (CDCl$_3$) δ ppm = 8.67 (br. s., 2 H), 8.36-8.34 (m, 2 H), 7.57-7.49 (m, 2 H), 7.45-7.31 (m, 1H), 7.20-7.17 (m, 1 H,), 6.69-6.67 (m, 1 H), 4.64 (m 1 H), 3.75-3.59 (m, 1 H), 3.56-3.45 (m, 1 H), 2.49 (m, 1 H), 2.12-2.03 (m, 1H), 1.85-1.65 (m, 3H), 1.61-1.40 (m, 1H), 1.18-1.02 (m, 1H), 0.63-0.01 (m, 1H), −.007- −0.87 (m, 1H).
ESI+ m/z 488 [M + H]$^+$ (5-chloro-2-(pyrimidin-2-yl)phenyl)((1S,3S,6R)-3-(((5-(trifluoromethyl)pyridin-2-yl)amino)methyl)-2-azabicyclo[4.1.0]heptan-2-yl)methanone -continued

| Comp. | Intermediate | Procedure | Yield % |
|---|---|---|---|
| 4c | (D56) | 27 | 11 |

¹H NMR (CDCl₃) δ ppm = 8.73 (br. s., 2 H), 8.53 (d, J = 8 Hz,1 H), 8.35 (s, 1 H),7.82 (dd, J = 8 Hz, 2 Hz, 1H), 7.72 (m, 1 H,), 7.56 (dd, J = 8 Hz, 2 Hz, 1 H), 7.27 (m, 1 H, under solvent peak), 6.67 (d, J = 8 Hz, 1 H), 4.61 (m, 1 H), 3.73-3.62 (m, 1H), 3.55-3.49 (m, 1H), 2.53-2.36 (m, 1H), 2.14-2.09 (m, 1H), 1.87-1.66 (m, 3H), 1.60-1.42 (m, 1H), 1.21-1.08 (m, 1H), 0.60--0.04 ((m, 1H), -0.10--1.01 (m, 1H).
ESI+ m/z 479 [M + H]⁺

(5-chloro-2-(pyrimidin-2-yl)phenyl)((1S,3S,6R)-3-(((4-(trifluoromethyl)pyridin-2-yl)amino)methyl)-2-azabicyclo[4.1.0]heptan-2-yl)methanone

| | | | |
|---|---|---|---|
| 4e | (D60) | 29 | 12 |

¹H NMR (CDCl₃) δ ppm = 8.68 (br. s., 2 H), 8.36-8.34 (m, 1 H), 8.04-8.05 (m, 1H), 7.52-7.49 (m, 1 H), 7.44-7.31 (m, 2H), 7.20-7.18 (m, 1 H,), 6.66-6.64 (m, 1 H), 4.64 (m, 1 H), 3.71-3.56 (m, 1 H), 3.42-3.36 (m, 1 H), 2.56-2.41 (m, 1H), 2.13-2.03 (m, 1H), 1.86-1.64 (m, 3H), 1.54-1.40 (m, 1H), 1.22-1.02 (m, 1H), 0.61-0.02 (m, 1H), -.01--1.05 (m, 1H).
ESI+ m/z 454 [M + H]⁺

(5-chloro-2-(pyrimidin-2-yl)phenyl)((1S,3S,6R)-3-(((5-chloropyridin-2-yl)amino)methyl)-2-azabicyclo[4.1.0]heptan-2-yl)methanone

| | | | |
|---|---|---|---|
| 4f | (D59) | 29 | 47 |

¹H NMR (CDCl₃) δ ppm = 8.62 (br. s., 2 H), 8.28-8.23 (m, 2 H), 7.35-7.33 (m,1H), 7.25-7.07 (m, 2 H), 6.75-6.71 (m, 2H), 4.76 (m, 1 H), 3.67-3.50 (m, 2 H), 2.60-2.45 (m, 4 H), 2.11-2.02 (m, 1H), 1.85-1.66 (m, 2H), 1.57-1.44 (m, 2H, under water peak), 1.13-0.98 (m, 1H), 0.57-0.01 (m, 1H), -0.24--0.95 (m, 1H).
ESI+ m/z 468 [M + H]⁺

(5-methyl-2-(pyrimidin-2-yl)phenyl)((1S,3S,6R)-3-(((4-(trifluoromethyl)pyridin-2-yl)amino)methyl)-2-azabicyclo[4.1.0]heptan-2-yl)methanone

| | | | |
|---|---|---|---|
| 4g | (D62) | 29 | 30 |

¹H NMR (CDCl₃) δ ppm = 8.66 (br. s., 2 H), 8.27-8.25 (m, 1 H), 8.05-8.02 (m, 1H), 7.37-7.33 (m, 2H), 7.25-7.13 (m, 2 H), 6.75-6.66 (m, 1H), 4.69 (m, 1 H), 3.67-3.52 (m, 1 H), 3.41-3.35 (m, 1H), 2.52-2.45 (m, 4 H), 2.10-2.02 (m, 1H), 1.84-1.80 (m, 1H), 1.75-1.55 (m, 3H), 1.12-0.98 (m, 1H), 0.66-0.01 (m, 1H), -0.21--0.82 (m, 1H).
ESI+ m/z 434 [M + H]⁺

((1S,3S,6R)-3-(((5-chloropyridin-2-yl)amino)methyl)-2-azabicyclo[4.1.0]heptan-2-yl)(5-methyl-2-(pyrimidin-2-yl)phenyl)methanone

| Comp. | Intermediate | Procedure | Yield % |
|---|---|---|---|
| 4h | (D63) | 29 | 44 |

¹H NMR (CDCl₃) δ ppm = 8.81 (m, 2 H), 8.50 (d, J = 4 Hz, 1 H), 8.36 (d, J = 8 Hz, 1H), 7.50 (dd, J = 8 Hz, 4 Hz, 1H), 7.23 (m, 1H), 6.83 (d, J = 4 Hz, 1 H), 6.18 (m, 1 H), 4.49 (m, 1H), 3.84-3.63 (m, 2 H), 2.49 (m, 1H), 2.10-1.99 (m, 1H), 1.79-1.51 (m, 3H, under solvent peak), 1.10 (m, 1H), 0.66-0.01 (m, 1H), −0.19-−0.72 (m, 1H).
ESI+ m/z 489 [M + H]⁺

(5-chloro-2-(pyrimidin-2-yl)phenyl)((1S,3S,6R)-3-(((4-(trifluoromethyl)pyrimidin-2-yl)amino)methyl)-2-azabicyclo[4.1.0]heptan-2-yl)methanone

| 4i | (D64) | 29 | 34 |
|---|---|---|---|

¹H NMR (CDCl₃) δ ppm = 8.81 (m, 2 H), 8.50 (d, J = 4 Hz, 1 H), 8.28 (d, J = 8 Hz, 1H), 7.33 (d, J = 8 Hz, 1H), 7.18 (m, 1 H), 6.83 (d, J = 4 Hz, 1 H), 6.28 (m, 1 H), 4.53 (m, 1H), 3.82-3.67 (m, 2 H), 2.53-2.49 (m, 4H), 2.08-1.97 (m, 1H), 1.79-1.52 (m, 3H, under solvent peak), 1.04 (m, 1H), 0.60-0.04 (m, 1H), −0.09-−0.80 (m, 1H).
ESI+ m/z 469 [M + H]⁺

(5-methyl-2-(pyrimidin-2-yl)phenyl)((1S,3S,6R)-3-(((4-(trifluoromethyl)pyrimidin-2-yl)amino)methyl)-2-azabicyclo[4.1.0]heptan-2-yl)methanone

Example 5

Preparation of Compound 5a (2-methyl-5-phenylthiazol-4-yl)((1S,3S,6R)-3-(((5-(trifluoromethyl)pyridin-2-yl)amino)methyl)-2-azabicyclo[4.1.0]heptan-2-yl)methanone

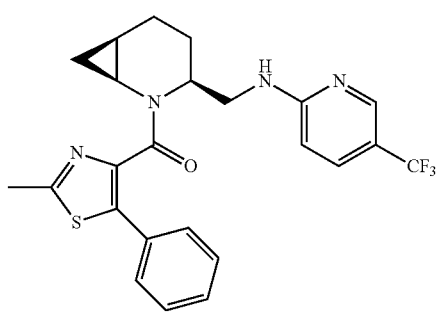 [SMILES: Cc1nc(C(=O)N2[C@H](CNc3ccc(C(F)(F)F)cn3)CC[C@@H]3C[C@@H]32)c(-c2ccccc2)s1]

D65 (12 mg, 0.06 mmol), N-methyl-morpholine (22 μL, 0.20 mmol) and 2-chloro-4,6-dimethoxy-1,3,5-triazine (12 mg, 0.06 mmol) dissolved in dry 1,4-dioxane (0.5 mL) were stirred at 25° C. for 0.5 hour, then D52 (18 mg, 0.06 mmol) dissolved in 1,4-dioxane (0.5 mL) was added. The reaction mixture was heated overnight at 60° C., cooled to RT and purified by silica gel column chromatography (Cyclohexane to AcOEt). The residue was dissolved in DCM, washed with an aqueous saturated solution of NaHCO₃ and concentrated to give the title compound. Yield (21 mg, 77%)

¹H NMR (CDCl₃) δ ppm 8.35 (m, 1H), 7.56 (m, 1H), 7.46 (m, 2H), 7.30-7.32 (m, 1H), 7.19 (m, 2H), 6.62 (m, 1H), 6.11 (m, 1H), 4.62 (m, 1H), 3.56-3.62 (m, 1H), 3.35-3.43 (m, 1H), 2.77 (s, 3H), 2.66 (m, 1H), 2.01 (m, 1H), 1.67-1.76 (m, 2H), 1.43-1.51 (m, 1H), 1.07 (m, 1H), 0.34 (m, 1H), −0.21 (m, 1H).
ESI+ m/z 472 [M+H]⁺

BIOLOGICAL SECTION

In a typical experiment, the antagonistic activity against human OX1 and OX2 receptors is determined by using CHO e HEK-293 cells transfected with human recombinant OX1 and OX2 receptors respectively, seeded at density of 2 and 3×10⁴ cells/well respectively in a 96 fluorimetry well plate. Thus the plate was loaded with the calcium dye (Fluo-4NW/probenecid in HBSS, Hepes 20 mM, pH 7,4; Invitrogen) at 37° C. for 60 min. Afterward the temperature was equilibrated at 22° C. for 15 min and the [Ca2+]i measured directly on the plate by using a fluorescent plate reader (CellLux Perkin Elmer).

Invention compounds were dissolved in DMSO, diluted in HBSS (DMSO, 0.3% final) and added to the wells. After 5 min CHO cells were activated with orexin-A, 3 nM while HEK-293 cells were activated with orexin-B, 10 nM.

The compounds, dissolved in DMSO and diluted in the medium (DMSO, 0.3% final), have been analysed in the 1 nM-1 μM concentration range (every concentration in duplicate). The antagonistic activity has been expressed as pKb (co-logarithm of the apparent dissociation constant calculated by using the modified Cheng Prusoff equation).

The results are expressed as percent of control specific antagonist response ((measured specific response/control specific agonist response)×100) obtained in the presence of the test compounds.

The $IC_{50}$ values (concentration causing a half-maximal inhibition of the control specific agonist response) were determinated by non-linear regression analysis of the concentration curves generated with mean replicate values using hill equation curve fitting. The $IC_{50}$ values are obtained by the arithmetical mean of at least two experiments.

Compounds of the following example tested according to this example gave pKbs as follows:

| Compound | pKb OX1 | pKb OX2 |
|---|---|---|
| 1a | 8.8 | 8.4 |
| 1b | 8.3 | 8.0 |
| 1c | 9.1 | 7.9 |
| 1d | 8.9 | 8.4 |
| 1e | 8.6 | 7.9 |
| 1f | 9.1 | 7.8 |
| 1g | 9.0 | 8.3 |
| 1h | 8.1 | 8.0 |
| 1i | 8.8 | 7.7 |
| 1j | 8.3 | 7.7 |
| 1k | 8.6 | 8.3 |
| 2a | 8.6 | 8.6 |
| 2b | 8.9 | 7.8 |
| 2c | 8.9 | 8.2 |
| 3a | 8.9 | 7.2 |
| 3b | 7.1 | 5.0 |
| 3c | 7.9 | 7.2 |
| 3d | 8.9 | 7.7 |
| 3e | 9.0 | 7.8 |
| 3f | 9.0 | 7.3 |
| 3g | 8.8 | 7.9 |
| 4a | 8.6 | 7.4 |
| 4b | 8.3 | 6.7 |
| 4c | 8.2 | 7.1 |
| 4d | 8.1 | 7.3 |
| 4e | 8.4 | 5.0 |
| 4f | 8.2 | 7.4 |
| 4g | 8.8 | 5.0 |
| 4h | 7.5 | 5.0 |
| 4i | 7.6 | 5.0 |
| 5a | 8.6 | 7.3 |

The invention claimed is:

1. A compound of formula (II) or a pharmaceutically acceptable salt thereof:

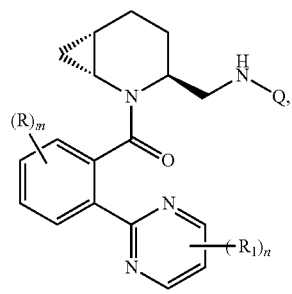

(II)

wherein

Q is 5-6 membered heteroaryl group, which may be substituted by one or more substituents independently selected from: C1-C4 alkyl, halogen, halo C1-C4 alkyl, C1-C4 alkoxy, or CN;

R and $R_1$ are independently selected from: C1-C4 alkyl, halogen, halo C1-C4 alkyl, C1-C4 alkoxy, or CN;

m is 0, 1, 2, 3, or 4; and n is 1, 2, or 3.

2. A compound of formula (III) or a pharmaceutically acceptable salt thereof:

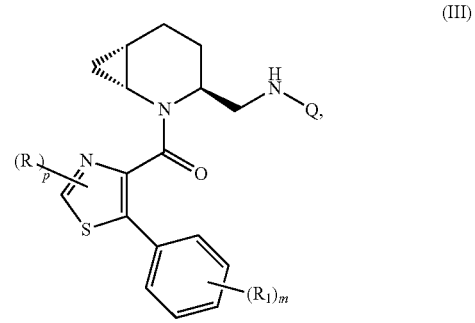

(III)

wherein

Q is 5-6 membered heteroaryl group, which may be substituted by one or more substituents independently selected from: C1-C4 alkyl, halogen, halo C1-C4 alkyl, C1-C4 alkoxy, or CN;

R and $R_1$ are independently selected from: C1-C4 alkyl, halogen, halo C1-C4 alkyl, C1-C4 alkoxy, or CN;

m is 0, 1, 2, 3, or 4; and

P is 0 or 1.

3. A compound of formula (V) or a pharmaceutically acceptable salt thereof:

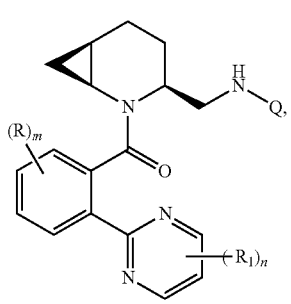

(V)

wherein

Q is 5-6 membered heteroaryl group, which may be substituted by one or more substituents independently selected from: C1-C4 alkyl, halogen, halo C1-C4 alkyl, C1-C4 alkoxy, or CN;

R and $R_1$ are independently selected from: C1-C4 alkyl, halogen, halo C1-C4 alkyl, C1-C4 alkoxy, or CN;

m is 0, 1, 2, 3, or 4;

n is 1, 2, or 3.

4. A compound of formula (VI) or a pharmaceutically acceptable salt thereof:

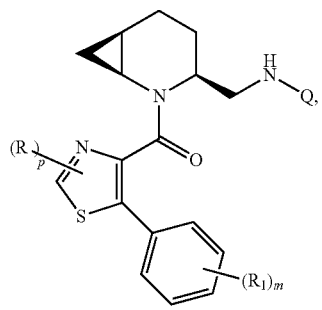

(VI)

wherein
Q is 5-6 membered heteroaryl group, which may be substituted by one or more substituents independently selected from: C1-C4 alkyl, halogen, halo C1-C4 alkyl, C1-C4 alkoxy, or CN;
R and $R_1$ are independently selected from: C1-C4 alkyl, halogen, halo C1-C4 alkyl, C1-C4 alkoxy, or CN;
m is 0, 1, 2, 3, or 4; and
p is 0 or 1.

5. A compound, wherein the compound is:
(5-chloro-2-(pyrimidin-2-yl)phenyl)((1R,3S,6S)-3-(((4-(trifluoromethyl)pyridin-2-yl)amino)methyl)-2-azabicyclo[4.1.0]heptan-2-yl)methanone;
4-(pyrimidin-2-yl)-3-((1R,3S,6S)-3-4(5-(trifluoromethyl)pyridin-2-yl)amino)methyl)-2-azabicyclo[4.1.0]heptane-2-carbonyl)benzonitrile;
((1R,3S,6S)-3-(((5-chloropyridin-2-yl)amino)methyl)-2-azabicyclo[4.1.0]heptan-2-yl)(5-methyl-2-(pyrimidin-2-yl)phenyl)methanone;
(5-methyl-2-(pyrimidin-2-yl)phenyl)((1R,3S,65)-3-4(5-(trifluoromethyl)pyridin-2-yl)amino)methyl)-2-azabicyclo[4.1.0]heptan-2-yl)methanone;
(5-chloro-2-(pyrimidin-2-yl)phenyl)((1R,3S,65)-3-4(5-(trifluoromethyl)pyridin-2-yl)amino)methyl)-2-azabicyclo[4.1.0]heptan-2-yl)methanone;
(5-chloro-2-(pyrimidin-2-yl)phenyl)((1R,3S,65)-3-4(5-chloropyridin-2-yl)amino)methyl)-2-azabicyclo[4.1.0]heptan-2-yl)methanone;
(5-chloro-2-(pyrimidin-2-yl)phenyl)((1R,3S,65)-3-4(4-(trifluoromethyl)pyridin-2-yl)amino)methyl)-2-azabicyclo[4.1.0]heptan-2-yl)methanone;
4-(pyrimidin-2-yl)-3-((1R,3S,65)-3-4(4-(trifluoromethyl)pyridin-2-yl)amino)methyl)-2-azabicyclo[4.1.0]heptane-2-carbonyl)benzonitrile;
3-((1R,3S,65)-3-(((5-chloropyridin-2-yl)amino)methyl)-2-azabicyclo[4.1.0]heptane-2-carbonyl)-4-(pyrimidin-2-yl)benzonitrile;
4-(pyrimidin-2-yl)-3-((1R,3S,6S)-3-4(4-(trifluoromethyl)pyrimidin-2-yl)amino)methyl)-2-azabicyclo[4.1.0]heptane-2-carbonyl)benzonitrile;
(5-methyl-2-(pyrimidin-2-yl)phenyl)((1R,3S,6S)-3-4(4-(trifluoromethyl)pyrimidin-2-yl)amino)methyl)-2-azabicyclo[4.1.0]heptan-2-yl)methanone;
(2-methyl-5-phenylthiazol-4-yl)((1R,3S,6S)-3-4(5-(trifluoromethyl)pyridin-2-yl)amino)methyl)-2-azabicyclo[4.1.0]heptan-2-yl)methanone;
((1R,3S,6S)-3-(((5-chloropyridin-2-yl)amino)methyl)-2-azabicyclo[4.1.0]heptan-2-yl)(2-methyl-5-phenylthiazol-4-yl)methanone;
(2-methyl-5-phenylthiazol-4-yl)((1R,3S,6S)-3-((4-(trifluoromethyl)pyridin-2-yl)amino)methyl)-2-azabicyclo[4.1.0]heptan-2-yl)methanone;
(5-methyl-2-(pyrimidin-2-yl)phenyl)((1S,3 S,6R)-3-(((5-(trifluoromethyl)pyridin-2-yl)amino)methyl)-2-azabicyclo[4.1.0]heptan-2-yl)methanone;
(5-chloro-2-(pyrimidin-2-yl)phenyl)((1S,3S,6R)-3-4(5-(trifluoromethyl)pyridin-2-yl)amino)methyl)-2-azabicyclo[4.1.0]heptan-2-yl)methanone;
4-(pyrimidin-2-yl)-3-((1S,3 S,6R)-3-(((5-(trifluoromethyl)pyridin-2-yl)amino)methyl)-2-azabicyclo[4.1.0]heptane-2-carbonyl)benzonitrile;
(5-chloro-2-(pyrimidin-2-yl)phenyl)((1S,3S,6R)-3-4(4-(trifluoromethyl)pyridin-2-yl)amino)methyl)-2-azabicyclo[4.1.0]heptan-2-yl)methanone;
(5-chloro-2-(pyrimidin-2-yl)phenyl)((1S,3S,6R)-3-4(5-chloropyridin-2-yl)amino)methyl)-2-azabicyclo[4.1.0]heptan-2-yl)methanone;
(5-methyl-2-(pyrimidin-2-yl)phenyl)((1S,3S,6R)-3-4(4-(trifluoromethyl)pyridin-2-yl)amino)methyl)-2-azabicyclo[4.1.0]heptan-2-yl)methanone;
((1S,3S,6R)-3-(((5-chloropyridin-2-yl)amino)methyl)-2-azabicyclo[4.1.0]heptan-2-yl)(5-methyl-2-(pyrimidin-2-yl)phenyl)methanone;
(5-chloro-2-(pyrimidin-2-yl)phenyl)((1S,3S,6R)-3-(((4-(trifluoromethyl)pyridin-2-yl)amino)methyl)-2-azabicyclo[4.1.0]heptan-2-yl)methanone;
(5-methyl-2-(pyrimidin-2-yl)phenyl)((1S,3S,6R)-3-(((4-(trifluoromethyl)pyridin-2-yl)amino)methyl)-2-azabicyclo[4.1.0]heptan-2-yl)methanone; or
(2-methyl-5-phenylthiazol-4-yl)((1S,3S,6R)-3-(((4-(trifluoromethyl)pyridin-2-yl)amino)methyl)-2-azabicyclo[4.1.0]heptan-2-yl)methanone;
or a pharmaceutically acceptable salt thereof.

6. A method for treating obesity, sleep disorders, compulsive disorders, substance abuse, or schizophrenia comprising administering to a subject in need thereof an effective amount of a compound as in any one of claims 1, 2, 3, 4, and 5 or a pharmaceutically acceptable salt thereof.

7. A pharmaceutical composition comprising a compound as in any one of claims 1, 2, 3, 4, and 5 or a pharmaceutically acceptable salt thereof and a pharmaceutically acceptable carrier.

\* \* \* \* \*